United States Patent [19]

Ashe et al.

[11] Patent Number: 5,699,270
[45] Date of Patent: Dec. 16, 1997

[54] METHOD FOR PREPARING LUBRICATION OILS (LAW232)

[75] Inventors: Terrence Rodney Ashe, Point Edward; Ross William Kapala; Stilianos George Roussis, both of Brights Grove, all of Canada

[73] Assignee: Exxon Research and Engineering Company, Florham Park, N.J.

[21] Appl. No.: 494,643

[22] Filed: Jun. 23, 1995

[51] Int. Cl.$^6$ ............................................. G01J 3/42
[52] U.S. Cl. .............................. 364/500; 208/49; 208/78
[58] Field of Search .............................. 364/500, 496, 364/497, 498, 499; 395/906, 904; 436/29, 60; 208/49, 78

[56] References Cited

U.S. PATENT DOCUMENTS

| | | | |
|---|---|---|---|
| 4,800,279 | 1/1989 | Hieftje et al. | 250/339.12 |
| 5,119,315 | 6/1992 | Kemp et al. | 364/498 |
| 5,121,337 | 6/1992 | Brown | 364/498 |
| 5,218,529 | 6/1993 | Meyer et al. | 364/413.01 |
| 5,360,972 | 11/1994 | DiFoggio et al. | 364/498 |
| 5,412,581 | 5/1995 | Tackett | 364/497 |
| 5,424,959 | 6/1995 | Reyes et al. | 364/498 |
| 5,446,681 | 8/1995 | Gethner et al. | 364/498 |
| 5,452,232 | 9/1995 | Espinosa et al. | 364/498 |

FOREIGN PATENT DOCUMENTS

| | | | |
|---|---|---|---|
| HEI 3-100463 | 4/1991 | Japan | 33/22 |

*Primary Examiner*—Emanuel T. Voeltz
*Assistant Examiner*—Kyle J. Choi
*Attorney, Agent, or Firm*—James H. Takemoto

[57] ABSTRACT

A method for controlling the manufacture of lubricating oils involving the steps of distillation, extracting, dewaxing and optionally hydrofining; or for controlling operating units associated with refinery or chemical processes with feed stocks and products boiling above 350° C. The method comprises selecting one or more chemical or perceptual or physical or performance properties of the lubricating oil or the feedstock, distillate or raffinate used in the manufacturing process; or of the refinery or chemical process feed stocks or products; creating a training set from reference samples which contain characteristic molecular species present in the lubricating oil, feedstock, distillate or raffinate used in the manufacturing process or from the refining or chemical operations. The reference samples are subjected to GC/MS analysis wherein the often collinear data generated is treated by multivariate correlation methods. The training set produces coefficients which are multiplied by the matrix generated from a GC/MS analysis of an unknown sample to produce a predicted value of the chemical, performance, perceptual or physical property or groups of properties selected.

11 Claims, 1 Drawing Sheet

METHOD FOR PREPARING LUBRICATION OILS (LAW232)

BACKGROUND OF THE INVENTION

1. Field of the Invention

This invention relates to a method for preparing lubricating oils by predicting performance, perceptual, chemical or physical properties of streams entering or exiting units in the lubes manufacturing process using a combination of gas chromatography and mass spectrometry.

2. Description of the Related Art

Refineries and chemical plants typically control processing of various component streams and certain additives through the use of both on-line analyzers and off-line laboratory analyses to provide quality information. These quality parameters (chemical composition, physical or perceptual or performance properties) are then fed back into a process control computer which contains control software or algorithms which control refinery or chemical plant hardware (distillation towers or proportional flow control valves). The control programs are typically executed more than three times per hour and their output is used to control either processes or proportional flow valves to vary the quality of the finished product which can either go to tankage or directly to pipelines and terminals, trucks, or to ship-loading facilities. Multiple on-line analyzers are typically required for this process control.

Gas chromatography has been used to predict physical and performance properties of hydrocarbon mixtures boiling in the gasoline range. Crawford and Hellmuth, Fuel, 1990, 69, 443–447, describe the use of gas chromatography and principal components regression analysis to predict the octane values for gasolines blended from different refinery streams. Japanese laid-open patent application JP 03-100463 relates to a method of estimating the cetane number for fuel oils by separating an oil sample into its components using gas chromatography, measuring the signal strength of ion intensities at characteristic masses in the mass spectrum, and correlating these ion intensities to cetane number using multiple regression analysis.

Combined gas chromatography/mass spectrometry (GS/MS) analysis has been done on crude oils. U.S. Pat. No. 5,119,315 discloses a method for aligning sample data such as a mass chromatogram with reference data from a known substance. Williams et al, 12th European Assoc. Organic Geochem., Organic Geochem. Int. Mtg. (Germany 09/16–20/85); Organic Geochemistry 1986, Vol. 10 (1–3) 451–461, discusses the biodegradation of crude oils as measured by GC/MS analysis.

It would be desirable to have a single analyzer means for rapidly measuring chemical or physical properties of intermediate streams in the manufacturing process and/or lube oil products and using these properties to control units within the manufacturing process and/or product quality.

SUMMARY OF THE INVENTION

This invention relates to a process for controlling the manufacture of lubricating oils from a feed having a boiling point of about 350° C. or greater by the steps of introducing the feed into a distillation unit, separating the feed into light, medium and heavy distillates, introducing the distillates into an extraction unit, extracting the distillates to produce raffinates, introducing the raffinates into a dewaxing unit and dewaxing the raffinates to produce lubricating oils, said process comprising:

(a) obtaining samples of at least one of lubricating oil, feed, distillate and raffinate;

(b) selecting at least one physical, chemical, perceptual or performance property of at least one of lubricating oil, feed, distillate and raffinate;

(c) selecting reference samples, said reference samples containing characteristic compound types present in the at least one lubricating oil, feed, distillate and raffinate and which have known values for the property or properties selected in step (b);

(d) producing a training set by the steps of:
  (1) injecting each reference sample into a gas chromatograph which is interfaced to a mass spectrometer thereby causing at least a partial separation of the hydrocarbon mixture into constituent chemical components;
  (2) introducing the constituent chemical components of each reference sample into the mass spectrometer, under dynamic flow conditions;
  (3) obtaining for each reference sample a series of time resolved mass chromatograms;
  (4) calibrating the mass chromatograms to correct retention times;
  (5) selecting a series of corrected retention time windows;
  (6) selecting within each retention time window a series of molecular and/or fragment ions, said ions being representative of characteristic compounds or compound classes expected within the retention time window;
  (7) recording the total amount of each characteristic compound or compound group selected in step d(6);
  (8) forming the data from steps d(6) and d(7) into a X-block matrix;
  (9) forming the property data selected in (a) for reference samples selected in (b) into a Y-block matrix;
  (10) analyzing the data from steps d(8) and d(9) by multivariate correlation techniques including Partial Least Squares, Principal Component Regression, or Ridge Regression to produce a series of coefficients;

(e) subjecting at least one unknown sample of at least one of lubricating oil, feed, distillate and raffinate to steps d(1) to d(3) in the same manner as the reference sample to produce a series of time resolved mass chromatograms;

(f) repeating steps d(4) and d(8) for each mass chromatogram from step (e);

(g) multiplying the matrix from step (f) by the coefficients from step d(10) to produce a predicted value for the property or properties of the at least one lubricating oil, and/or at least one feed, distillate and raffinate sample or samples; and (h) using the predicted values of the property or properties of the lubricating oil and/or at least one of the feed, distillate and raffinate sample or samples to control operation of at least one of the distillation unit, extraction unit and dewaxing unit.

Another embodiment of the invention relates to a method for controlling or monitoring chemical or refinery processes which utilize feedstocks and/or produce products having boiling points greater than about 350° C. which comprises (a) obtaining at least one sample of a refinery or chemical feedstock or product;

(b) selecting at least one physical, chemical, perceptual or performance property of at least one refinery or chemical process feedstock or product;

(c) selecting reference samples, said reference samples containing characteristic compound types present in the at least one refinery or chemical process feedstock or product and which have known values for the property or properties selected in step (b);

(d) producing a training set by the steps of:
(1) injecting each reference sample into a gas chromatograph which is interfaced to a mass spectrometer thereby causing at least a partial separation of the hydrocarbon mixture into constituent chemical components;
(2) introducing the constituent chemical components of each reference sample into the mass spectrometer, under dynamic flow conditions;
(3) obtaining for each reference sample a series of time resolved mass chromatograms;
(4) calibrating the mass chromatograms to correct retention times;
(5) selecting a series of corrected retention time windows;
(6) selecting within each retention time window a series of molecular and/or fragment ions, said ions being representative of characteristic compounds or compound classes expected within the retention time window;
(7) recording the total amount of each characteristic compound or compound group selected in step d(6);
(8) forming the data from steps d(6) and d(7) into a X-block matrix;
(9) forming the property data selected in (a) for reference samples selected in (b) into a Y-block matrix;
(10) analyzing the data from steps d(8) and d(9) by multivariate correlation techniques including Partial Least Squares, Principal Component Regression, or Ridge Regression to produce a series of coefficients;

(e) subjecting at least one unknown refinery or chemical process feedstock or process sample to steps d(1) to d(3) in the same manner as the reference samples to produce a series of time resolved mass chromatograms;

(f) repeating steps d(4) and d(8) for each mass chromatogram from step (e); (g) multiplying the matrix from step (f) by the coefficients from step d(10) to produce a predicted value of the property or properties for the refinery or chemical process feedstocks or products sample or samples; and (h) using the predicted values of the property or properties of the refinery or chemical feedstocks, intermediate or products sample or samples to control the refinery or chemical process.

The gas chromatography/mass spectrometry (GC/MS) method described above can be used to rapidly predict a wide range of perceptual, performance, chemical and/or physical properties of complex mixtures such as intermediate streams in the lubes manufacturing process and lubricating oil products. Such properties include distillation characteristics, pour point, density, aniline point, feed stock quality, cloud point, haze, viscosity and the like as well as specific chemical constituents. The multivariate correlation methods can also treat the collinear data generated by the GC/MS analyses.

DETAILED DESCRIPTION OF THE INVENTION

The typical lubricating oil manufacturing process involves a distillation unit, an extraction unit, a dewaxing unit and optionally, a hydrofining unit. The lubricating oil products are commonly used as base stocks for producing finished oils or may be specialty products such as transformer oils and agricultural oils.

Figure 1:
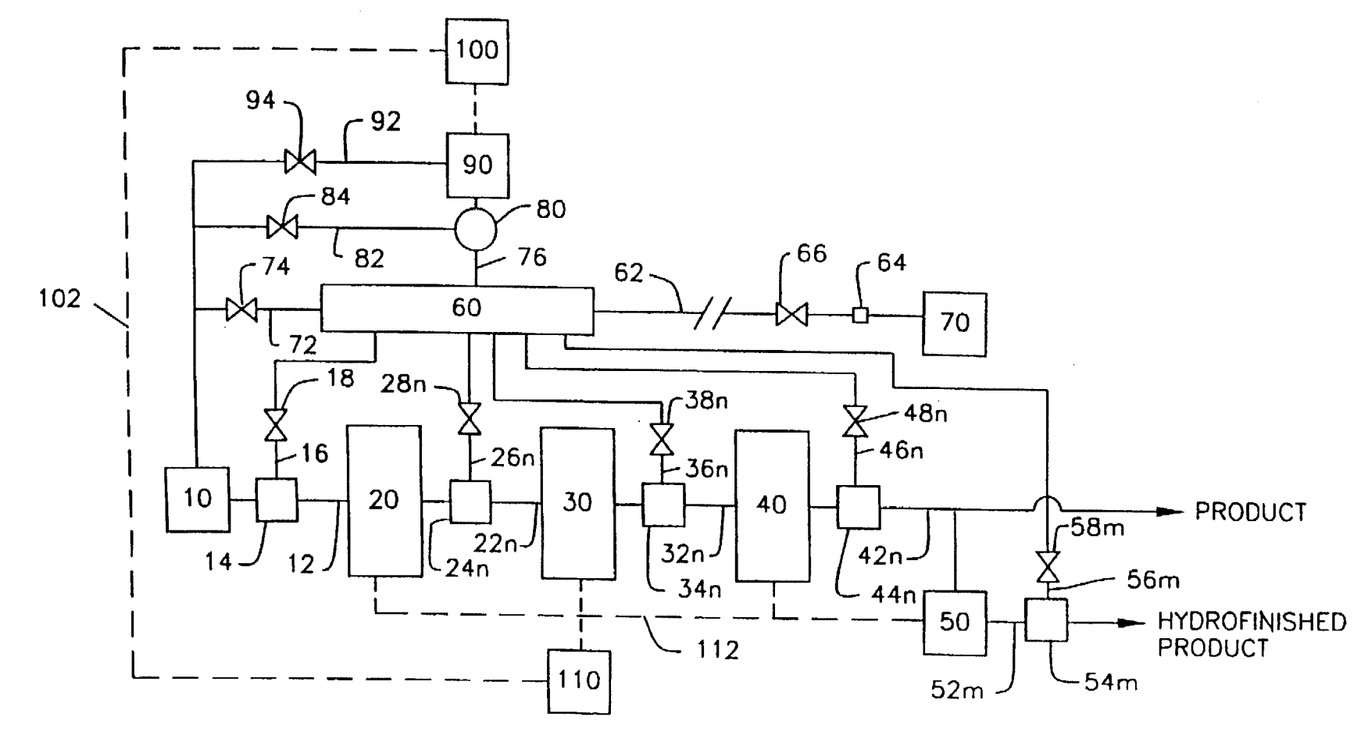
FIG. 1 is a schematic flow diagram of a manufacturing process for a lube oil.

FIG. 1 is a schematic flow diagram showing an on-line manufacturing process. Feed stocks 10 are complex hydrocarbon mixtures such as crudes or heavy distillate streams. The feedstock is fed to distillation unit 20 through line 12. Feedstock may be sampled through sampling port 14 which is connected to sampling line 16 interrupted by valve 18.

Distillation unit 20 is typically a pipestill which distills the feed stock into a plurality of distillation cuts. For purposes of simplicity, these distillation cuts are shown exiting unit 20 as line 22 which represents a plurality of lines where n is the number of distinct distillation cuts. Each of the lines 22n may be sampled through sampling ports 24n which are connected to sampling lines 26n interrupted by valves 28n.

The distillate cuts are fed to extraction unit 30 where they are extracted using solvents such as phenol, N-methylpyrrolidone and the like. The extraction process results in raffinates and bottoms. Again for purposes of simplicity, these raffinates are shown exiting the extraction unit 30 as a single line 32n which represents a plurality of lines where n is the number of different raffinate extracts. Each of the lines 32n may be sampled through sampling ports 34n which are connected to sampling lines 36n interrupted by valves 38n. The raffinate extracts are usually stripped of solvent in a stripping unit (not shown) prior to entering the dewaxing unit.

In the dewaxing unit 40, wax is removed by dewaxing aids such as methyl ethyl ketone, propane and the like. As in the previous units, for purposes of simplicity, the dewaxed raffinates are shown exiting the dewaxing unit 40 as a single line 42n where n is the number of dewaxed raffinates. Each of lines 42n may be sampled through sampling ports 44n which are connected to sampling lines 46n interrupted by valves 48n.

The dewaxed raffinates exiting unit 40 through lines 42n may be used as lubricating oils (following removal of dewaxing aid). Typical examples of such lube oils are known as light neutrals, heavy neutrals, bright stocks and the like. These lube oils may be sampled for product quality through sampling ports 44n connected to sampling lines 46n interrupted by valves 48n. These lube oils may optionally be subjected to a hydrofinishing step in a hydrofiner unit 50. Hydrofiners use catalysts and conditions well known in the art. The hydrofinished products exit hydrofiner 50 through lines 52m where m represents the number of lube oils subjected to hydrofinishing. The hydrofinished oils may be sampled through sampling ports 54m connected to sampling lines 56m interrupted by valves 58m.

Each of lines 16, 26n, 36n, 46n and 56m are connected to sampling manifold 60. Sampling manifold 60 also includes an optional provision for at-line operation wherein a remote location 70 is connected to the sampling manifold 60 through line 62 interrupted by valve 66 and sampling port 64. Sampling manifold 60 is a central location where all samples to be analyzed are gathered prior to GC/MS analysis. Manifold 60 can be purged by sample to be analyzed to remove contaminants and purged material recycled through line 72 interrupted by valve 74.

Sample to be analyzed is fed through line 76 to sample injection valve 80. Injection valve 80 can likewise be purged by sample to be analyzed through line 82 interrupted by valve 84. Once sample manifold 60 and sample injection valve 80 are purged, sample to be analyzed is injected into GC/MS analyzer. Samples from off-line operation can be directly injected through valve 80. Off-line samples are those collected at remote locations and brought to a central facility for analysis. The raw data generated by GC/MS analyzer 90 is fed to computer 100. Spent sample and purging materials are sent to recycle through line 92 interrupted by valve 94. Computer 100 mathematically treats raw GC/MS data. Output from computer 100 is then fed as an electronic signal through line 102 to control computer 110. Control computer 110 is connected through line 112 to units 20, 30, 40 and 50 and controls operating conditions within said units 20, 30, 40 and 50. The operating conditions in turn controls the quality of lube oil product exiting units 40 and/or 50.

The operation of the GC/MS analyzer 90 and computer 100 is described in further detail as follows. The feedstock, distillate cuts and lubricating oil products are all complex hydrocarbon mixtures involving thousands of individual chemical species. The use of GC/MS to analyze such complex mixtures for chemical and physical properties involves the generation of large amounts of collinear data. Multiple regression analysis may be employed for treating normal linear data. However, this type of analysis cannot be used for collinear data.

The process according to the invention involves a means for predicting chemical, performance, perceptual and physical properties of feedstock, distillates, raffinates and lubricating oils by quantitative identification of components using a combination of retention times from a GC analysis coupled with target fragment and/or molecular ions produced by the MS. The MS information is compared against a set of known properties from reference samples which form a training set. By mathematically comparing the experimental data with that of the training set, one may predict the desired properties of other feedstocks, distillates, raffinates and lubricating oils.

GC/MS utilizes a gas chromatograph interfaced with a mass spectrometer. While a chromatographic method such as supercritical fluid chromatography, liquid chromatography or size exclusion chromatography may be used to separate the mixture into components or mixtures of components, gas chromatography, especially capillary gas chromatography is the preferred means for interfacing with a mass spectrometer. Both GC and MS use computer software for instrument control, data acquisition and data reduction. The computer platform should be capable of acquiring at least 2000 mass spectra in about 7 minutes.

The sample mixture to be analyzed is first injected into a GC where the mixture components are separated as a function of retention time, often on the basis of boiling points. Only partial chromatographic resolution of mixture components is necessary. The GC oven temperature is usually programmed for samples with a wide boiling range. Separated components may also be identified by a detector such as a flame ionization detector, atomic emission detector, thermal conductivity detector or electron capture detector.

The separated or partially separated components are then transferred to the mass spectrometer under dynamic flow conditions. Since a GC operates under atmospheric pressure and a MS under vacuum conditions (about $10^{-3}$ kPa), the instrument interface requires a coupling device such as a molecular separator (e.g., jet, membrane, etc.), open split coupler or capillary direct interface to efficiently transfer sample while minimizing carrier gas effects.

Depending on the nature of the sample, the mixture may be introduced directly into a MS using a direct insertion probe without a prior GC separation step. Other thermal separation techniques not involving a GC may be used to introduce the sample into the mass spectrometer.

In the MS, sample molecules are bombarded with high energy electrons thereby creating molecular ions which fragment in a pattern characteristic of the molecular species involved. A continuous series of mass spectra are obtained over a scan range of at least 10 to at least 800 daltons. The mass spectral data may also be acquired under selected ion monitoring (SIM) mode. In the selected ion mode, care must be taken to select ions representative of the components of interest and to operate under repeatable conditions. A variety of MS instruments may be used including low resolution, high resolution, MS/MS (hybrid, triple quadrupole, etc.), ion cyclotron resonance and time of flight. Any ionization technique may be used, such as electron ionization, chemical ionization, multiphoton ionization, field desorption, field ionization, etc., provided that the technique provides either molecular or fragment ions which are suitable for use in the analysis procedure.

The results of sample analysis are a series of e mass spectra. The mass spectra are divided into n time intervals where n is an integer from 1 to l. At least one diagnostic ion is chosen from each of m time intervals where m is an integer from 1 to n. The term "diagnostic ion" refers to an ion which is representative of a compound, a chemical class or a performance, perceptual or physical property correlated thereto. Regardless of whether mass spectra are obtained in the scan or selected ion monitoring mode, it is important that the mass spectra be obtained under repeatable conditions.

If the mass spectral data are acquired in the scan mode, the mass range covered during acquisition should be sufficient to provide acquisition of all of the ions which could be used as diagnostic ions during mathematical treatment of each mass spectral scan. If the mass spectral data are acquired in the selected ion monitoring mode, then care must be taken that the ions selected for monitoring are suitable for use in measuring the components of interest.

The sample mass spectral data are then compared to mass spectral data from a series of reference samples with known performance, perceptual, physical and/or chemical properties. In order to compare reference mass spectral data with sample mass spectral data, it may be desirable to time align the sample data to help ensure the integrity of the comparison. There are commercially available computer programs for such data alignment, for example, Hewlett-Packard GC/MS software G 1034C version C.01.05.

The reference mass spectral data, and associated properties data, are arranged in matrix form for mathematical treatment as described below. In the case of chemical composition information, one matrix is formed of reference sample ion intensities at given masses and the other matrix contains known ion intensities for molecular fragment ions of known components. The training set for chemical composition data is thus made up of mass spectral data for different components characteristic of compounds or molecular series expected to be found in the sample mixtures. Similar training sets can be formed for other chemical or perceptual or performance or physical properties of interest. These training sets form one block or matrix of data (Y-block or properties matrix). The actual sample mass spectral data (which may have been time aligned) form the other block (X-block) or matrix of data. These two matrices are subjected to mathematical treatments known as Partial Least Squares (PLS), or Principal Component Regression (PCR), or Ridge Regression (RR) to obtain a mathematically describable relationship between the properties data and mass spectral data, known as a model. Coefficients provided by this model are mathematically combined with the suitably treated mass spectral data from samples with unknown desired properties to:

a) predict desired properties, b) assess the suitability of the model for such predictions, and c) diagnose the stability and general correctness of the process that yielded the mass spectral data PLS/PCR/RR are described in the literature, e.g., Wold S., A. Ruhe, H. Wold, and W. J. Dunn, "The Collinearity Problem in Linear Regression. The Partial Least Squares (PLS) Approach to Generalized Inverses", SIAM J. Sci. Stat. Comput., 1984 5(3), 735–743, or Geladi P., and B. R. Kowalki, "Partial Least Squares Regression: A Tutorial", Anal. Chim. Acta, 1986, 185, 1–17, or Hökuldsson A., "PLS Regression Methods", J. Chemometrics, 1988, 2, 211–228, or in many other articles in journals such as the Journal of Chemometrics or Intelligent Laboratory Systems; Frank, L and J. Friedman, "A Statistical View of Some Chemometrics Regression Tools", Technometrics, 1993, Vol. 35, No. 2; Jackson, J. E., "A User's Guide To Principal Components", Wiley-Interscience, New York, 1991; Montogomery, D. C. and E. A. Peck, "Introduction To Linear Regression Analysis", Wiley-Interscience, New York, 1990; and Martens, H., and T. Naes, "Multivariable Calibration", Wiley-Interscience, New York,1989.

When dealing with a complex mixture, it is necessary to select appropriate masses or groups of masses at specific retention times for a particular compound or classes of compounds. The selection of such masses is the basis for a set a rules which then forms the data for the training set. There are no set procedures for such a selection process. The researcher must select appropriate masses for compounds of interest. For example, feed stocks and lube oils contain a wide range of compound types such as paraffins, cycloparaffins, aromatics, and olefins. It is known that paraffinic hydrocarbons yield fragment ions at masses 43, 57, 71, 85, . . . daltons, and these masses may be used as diagnostic of this class of compounds. Moreover, when coupled with retention time data, it is possible to identify concentrations of specific compounds within this class of compounds. In a similar manner, training sets for other chemical, performance, perceptual or physical properties may be developed by correlating compositional data with other properties of interest, e.g., distillation characteristics, viscosities and viscosity index, volatility, refractive index and the like. The result of a mathematical treatment such as PLS/PCR/RR of the training set is a set of coefficients for the properties of interest.

These coefficients are then multiplied by the data matrix for the sample. The result is a prediction of the desired property or properties which information can be used to control operating conditions in the distillation unit, extraction unit, dewaxing unit and/or hydrofiner as well as control lube oil quality. Moreover, variances in properties serve to promptly alert operators of upsets/changes in operating conditions which could influence product quality. The method of the invention is further illustrated by the following examples.

EXAMPLE 1

The method for predicting the physical or chemical properties of a complex hydrocarbon mixture is demonstrated in this example using density at 15° C. as the specific property for purposes of illustration. The method is generally applicable to a range of other physical properties as well as performance or perceptual or chemical properties of such mixtures.

The initial consideration is to establish a set of standard GC/MS operating parameters so that the GC/MS analytical data used for predicting properties is obtained under consistent operating conditions. The GC/MS instrument used in this example is a Hewlett-Packard 5972 Mass Selective Detector interfaced to a Hewlett-Packard 5890 Series II Gas Chromatograph fitted for used with microbore columns.

The GC/MS operating conditions are summarized in Table 1.

TABLE 1

| GC Conditions | |
|---|---|
| Column | Phenyl Silicone (such as HP-5) 10 m × 0.1 mm, 17 micron film thickness |
| Temperature Profile | |
| Initial Temperature (°C.) | 180 |
| Initial Time (minutes) | 0 |
| Program Rate (°C./min.) | 15 |
| Final Temperature (°C.) | 310 |
| Final Time (minutes) | 5.33 |
| Pressure Program | |
| Initial Pressure (psi) | 30 |
| Initial Time (minutes) | 0 |
| Program Rate (psi/minute) | 4 |
| Final Pressure (psi) | 80 |
| Final Time (minutes) | 10 |
| Carrier Gas | Helium |
| Linear Velocity | approx. 25.6 |
| Injection Port Temperature (°C.) | 300 |
| Injection Volume, microliter | 0.5 |
| Split Ratio | 500:1 |
| Column Head Pressure, kPa | approx. 260 |
| Interface Temperature (°C.) | 310 |
| MS Conditions | |
| Ionization Mode | Electron Ionization, 70 eV, nominal |
| Mass Range Scanned (daltons) | 10–600 |
| Cycle Time (minutes) | 0.003 |

TABLE 2

CHEMST'S RULES FOR LUBES

| Rule[a] | Material[b] | | | Masses[c] | | | | Retention Time[d] | |
|---|---|---|---|---|---|---|---|---|---|
| | | | | | | | | Starting | Ending |
| 1 | nC16 | 43 | 57 | 71 | 85 | 99 | 113 | 1.00 | 1.89 |
| 2 | ½ Ring | 69 | 83 | 97 | 109 | 123 | 137 | 1.00 | 2.30 |
| 3 | ¾ Ring | 149 | 163 | 177 | 189 | 203 | 217 | 1.00 | 2.30 |
| 4 | ⅘ Ring | 229 | 243 | 257 | 269 | 283 | 297 | 1.00 | 2.30 |
| 5 | Ring | 309 | 223 | 337 | | | | 1.00 | 2.30 |
| 6 | −6 | 91 | 105 | 119 | 133 | 147 | 161 | 1.00 | 2.30 |
| 7 | −6.1 | 92 | 106 | 120 | 134 | 148 | 162 | 1.00 | 2.30 |
| 8 | −8/−10 | 115 | 117 | 129 | 131 | 143 | 145 | 1.00 | 2.30 |
| 9 | −12 | 128 | 141 | 142 | 155 | 156 | 169 | 1.00 | 2.30 |
| 10 | −14/−16 | 151 | 153 | 165 | 167 | 179 | 181 | 1.00 | 2.30 |
| 11 | −18 | 178 | 191 | 192 | 205 | 206 | 219 | 1.00 | 2.30 |
| 12 | −20 | 202 | 215 | 226 | 239 | 228 | 241 | 1.00 | 2.30 |
| 13 | nC17 | 43 | 57 | 71 | 85 | 99 | 113 | 1.89 | 1.98 |
| 14 | isoPara | 43 | 57 | 71 | 85 | 99 | 113 | 1.98 | 2.30 |
| 15 | nC18 | 43 | 57 | 71 | 85 | 99 | 113 | 2.30 | 2.40 |
| 16 | isoPara | 43 | 57 | 71 | 85 | 99 | 113 | 2.40 | 3.22 |
| 17 | ½ Ring | 69 | 83 | 97 | 109 | 123 | 137 | 2.40 | 3.22 |
| 18 | ¾ Ring | 149 | 163 | 177 | 189 | 203 | 217 | 2.40 | 3.22 |
| 19 | ⅘ Ring | 229 | 243 | 257 | 269 | 283 | 297 | 2.40 | 3.22 |
| . | . | . | . | . | . | . | . | . | . |
| . | . | . | . | . | . | . | . | . | . |
| . | . | . | . | . | . | . | . | . | . |
| 172 | −8/−10 | 115 | 117 | 129 | 131 | 143 | 145 | 12.07 | 14.00 |
| 173 | −12 | 128 | 141 | 142 | 155 | 156 | 169 | 12.07 | 14.00 |
| 174 | −14/−16 | 151 | 153 | 165 | 167 | 179 | 181 | 12.07 | 14.00 |
| 175 | −18 | 178 | 191 | 192 | 205 | 206 | 219 | 12.07 | 14.00 |
| 176 | −20 | 202 | 215 | 226 | 239 | 228 | 241 | 12.07 | 14.00 |
| 177 | nC39 | 43 | 57 | 71 | 85 | 99 | 113 | 12.83 | 12.87 |
| 178 | isoPara | 43 | 57 | 71 | 85 | 99 | 113 | 12.88 | 14.00 |

[a]Rule number, integer index
[b]Compound or group of compound rule applies to:
½ ring ½ ring cycloparaffins
¾ ring ¾ ring cycloparaffins
⅘ ring ⅘ ring cycloparaffins
6 ring 6 ring cycloparaffins
−6 $C_nH_{2n-6}$ alkylated benzenes
−6.1 $C_nH_{2n-6}$ LINEAR alkylated benzenes
−8/−10 $C_nH_{2n-8}$ alkylated indanes, $C_nH_{2n-10}$ alkylated indenes
−12 $C_nH_{2n-12}$ alkylated naphthalenes
−14/−16 $C_nH_{2n-14}$ alkylated acenaphthenes/$C_nH_{2n-16}$ alkylated acenaphthalenes
−18 $C_nH_{2n-18}$ alkylated phenanthrenes/anthracenes
−20 $C_nH_{2n-20}$ alkylated naphthenophenanthrenes
[c]Masses used in Rule [up to n may be specified,, where n is an integer which is equal to the number of masses scanned during the time interval (d)].
[d]Retention time for both starting and ending expected retention times based on historical averages in minutes.

TABLE 3

| MASS[a] | Reference Time[b] | Type[c] | Limit[d] | CalibTime[e] | Corr[f] |
|---|---|---|---|---|---|
| 268 | 2.800 | P | 0.15 | 2.794 | −0.006 |
| 282 | 3.276 | P | 0.15 | 3.272 | −0.004 |
| 366 | 6.260 | P | 0.15 | 6.266 | 0.006 |
| 422 | 7.953 | P | 0.15 | 7.953 | 0 |
| 57 | 10.556 | p | 0.15 | 10.591 | 0.035 |

[a]Mass or compound selected for the calibration
[b]Expected occurrence time, typically based on average of several analyses
[c]P = Peak or maximum occurrence, F = First occurrence of the material
[d]Range (± minutes) for reference compound
[e]Observed retention time for reference material
[f]Correction to be applied between reference materials (column a). Correction for first mass is from initial time to calibration time; correction for second mass is between first and second reference materials; and last correction is applied to end of data acquisition.

TABLE 4

| CHEMIST'S RULES FOR LUBES |
|---|

| | | | | | |
|---|---|---|---|---|---|
| Total Raw Abundance (TIC): | | | 770247450 | | |
| Chemist Rule: | | | 398341548 | | -51.72% |
| Air Leakage: | | | 247241 | | -0.03% |
| Average Scan Rate (Min/Max): | | | 292 | | (292/293) |
| Number of Records: | | | 2864 | | |

| Rule[a] | Compound[b] | Masses[c] | | | | | | Start[d] | End[e] | CStart[f] | Corr[g] | CEnd[h] | Corr[i] | Abundance[j] | |
|---|---|---|---|---|---|---|---|---|---|---|---|---|---|---|---|
| 1 | nC16 | 43 | 57 | 71 | 85 | 99 | 113 | 1.000 | 1.890 | 0.998 | -0.002 | 1.886 | -0.004 | 11823 | 0.00% |
| 2 | 1/2 ring | 69 | 83 | 97 | 109 | 123 | 137 | 1.000 | 2.300 | 0.998 | -0.002 | 2.295 | -0.005 | 32274 | 0.01% |
| 3 | 3/4 ring | 149 | 163 | 177 | 189 | 203 | 217 | 1.000 | 2.300 | 0.998 | -0.002 | 2.295 | -0.005 | 0 | 0.00% |
| 4 | 4/5 ring | 229 | 243 | 257 | 269 | 283 | 297 | 1.000 | 2.300 | 0.998 | -0.002 | 2.295 | -0.005 | 0 | 0.00% |
| 5 | 6 Ring | 309 | 223 | 337 | | | | 1.000 | 2.300 | 0.998 | -0.002 | 2.295 | -0.005 | 0 | 0.00% |
| 6 | -6 | 91 | 105 | 119 | 133 | 147 | 161 | 1.000 | 2.300 | 0.998 | -0.002 | 2.295 | -0.005 | 0 | 0.00% |
| 7 | -6.1 | 92 | 106 | 120 | 134 | 148 | 162 | 1.000 | 2.300 | 0.998 | -0.002 | 2.295 | -0.005 | 0 | 0.00% |
| 8 | -8/-10 | 115 | 117 | 129 | 131 | 143 | 145 | 1.000 | 2.300 | 0.998 | -0.002 | 2.295 | -0.005 | 0 | 0.00% |
| 9 | -12 | 128 | 141 | 142 | 155 | 156 | 169 | 1.000 | 2.300 | 0.998 | -0.002 | 2.295 | -0.005 | 0 | 0.00% |
| 10 | -14/-16 | 151 | 153 | 165 | 167 | 179 | 181 | 1.000 | 2.300 | 0.998 | -0.002 | 2.295 | -0.005 | 0 | 0.00% |
| 11 | -18 | 178 | 191 | 192 | 205 | 206 | 219 | 1.000 | 2.300 | 0.998 | -0.002 | 2.295 | -0.005 | 0 | 0.00% |
| 12 | -20 | 202 | 215 | 226 | 239 | 228 | 241 | 1.000 | 2.300 | 0.998 | -0.002 | 2.295 | -0.005 | 0 | 0.00% |
| 13 | nC17 | 43 | 57 | 71 | 85 | 99 | 113 | 1.890 | 1.980 | 1.886 | -0.004 | 1.976 | -0.004 | 83071 | 0.02% |
| 14 | isoPara | 43 | 57 | 71 | 85 | 99 | 113 | 1.980 | 2.300 | 1.976 | -0.004 | 2.295 | -0.005 | 163356 | 0.04% |
| 15 | nC18 | 43 | 57 | 71 | 85 | 99 | 113 | 2.300 | 2.400 | 2.295 | -0.005 | 2.395 | -0.005 | 417625 | 0.11% |
| 16 | isoPara | 43 | 57 | 71 | 85 | 99 | 113 | 2.400 | 3.220 | 2.395 | -0.005 | 3.216 | -0.004 | 3447651 | 0.87% |
| 17 | 1/2 ring | 69 | 83 | 97 | 109 | 123 | 137 | 2.400 | 3.220 | 2.395 | -0.005 | 3.216 | -0.004 | 1770916 | 0.45% |
| 18 | 3/4 ring | 149 | 163 | 177 | 189 | 203 | 217 | 2.400 | 3.220 | 2.395 | -0.005 | 3.216 | -0.004 | 1689 | 0.00% |
| 19 | 4/5 ring | 229 | 243 | 257 | 269 | 283 | 297 | 2.400 | 3.220 | 2.395 | -0.005 | 3.216 | -0.004 | 0 | 0.00% |
| . | . | . | . | . | . | . | . | . | . | . | . | . | . | . | . |
| . | . | . | . | . | . | . | . | . | . | . | . | . | . | . | . |
| 172 | -8/-10 | 115 | 117 | 129 | 131 | 143 | 145 | 12.070 | 14.000 | 12.105 | 0.035 | 14.035 | 0.035 | 0 | 0.00% |
| 173 | -12 | 128 | 141 | 142 | 155 | 156 | 169 | 12.070 | 14.000 | 12.105 | 0.035 | 14.035 | 0.035 | 0 | 0.00% |
| 174 | -14/-16 | 151 | 153 | 165 | 167 | 179 | 181 | 12.070 | 14.000 | 12.105 | 0.035 | 14.035 | 0.035 | 0 | 0.00% |
| 175 | -18 | 178 | 191 | 192 | 205 | 206 | 219 | 12.070 | 14.000 | 12.105 | 0.035 | 14.035 | 0.035 | 0 | 0.00% |
| 176 | -20 | 202 | 215 | 226 | 239 | 228 | 241 | 12.070 | 14.000 | 12.105 | 0.035 | 14.035 | 0.035 | 0 | 0.00% |
| 177 | nC39 | 43 | 57 | 71 | 85 | 99 | 113 | 12.830 | 12.870 | 12.865 | 0.035 | 12.905 | 0.035 | 7911 | 0.00% |
| 178 | isoPara | 43 | 57 | 71 | 85 | 99 | 113 | 12.880 | 14.000 | 12.915 | 0.035 | 14.035 | 0.035 | 106764 | 0.03% |
| | | | | | | | | | | | | | Sum = | 398341548 | 100.00% |

[a]Rule number, integer index
[b]Compound or group of compound rule applies to:
  1/2 ring    1/2 ring cycloparaffins
  3/4 ring    3/4 ring cycloparaffins
  4/5 ring    4/5 ring cycloparaffins
  6 ring    6 ring cycloparaffins
  -6    $C_nH_{2n-6}$ alkylated benzenes
  -6.1    $C_nH_{2n-6}$ linear alkylated benzenes
  -8/-10    $C_nH_{2n-8}$ alkylated indanes, $C_nH_{2n-10}$ alkylated indenes
  -12    $C_nH_{2n-12}$ alkylated naphthalenes
  -14/16    $C_nH_{2n-14}$ alkylated acenaphthenes/$C_nH_{2n-16}$ alkylated acenaphthalenes
  -18    $C_nH_{2n-18}$ alkylated phenanthrenes/anthracenes
  -20    $C_nH_{2n-20}$ alkylated naphthenophenanthrenes
[c]Masses used in Rule [up to n may be specified, where n is an integer which is equal to the number of masses scanned during the time interval (d to e) either in full scan mode or selected ion monitoring mode].
[d]Retention time for both starting and ending expected retention times based on historical averages in minutes.
[e]end retention time in minutes
[f]corrected start retention time
[g]correction = difference between start and cstart (in minutes)
[h]corrected end time
[i]correction = difference between end and cend (in minutes)
[j]Abunance, both as total sum and as normalized percentage based on Chemist's Rules.
Total Raw Abundance (TIC):    total area observed in the GC/MS analysis.
Chemist Rule:    total area found using the Chemist's Rules; based on experience, should be greater than 30% of total raw abundance.
Air Leakage:    total ionization due to air (m/z 28, 32, 40, 44) useful diagnostic for instrumentation problems.
Average Scan Rate (Min/Max):    shows the minimum, average and maximum scan rates during the GC/MS analysis and is a useful diagnostic to identify instrumental problems.
Number of records:    is the number of mass spectral scans acquired during the analysis.

The analysis summarized in Table 4 is done for each reference sample. The results from these respective analyses form a training set which is subjected to mathematical treatment. The goal is develop a model that can be used to predict the unknown properties of future samples using their mass spectral data only. The mathematical treatments are described by multivariate correlation techniques such as Projection to Latent Structures (PLS) or otherwise known as Partial Least Squares (PLS), Principal Component Regression (PCR), and Ridge Regression (RR). These techniques are superior to ordinary multiple linear regression in their ability to treat collinearity amongst variables in the X-block or GC/MS data matrix (and Y-block or properties matrix for PLS), and in their ability to handle the quantity of data generated by the Chemist's Rules. Ordinary Multiple Linear Regression cannot be used to treat collinear variables.

PLS/PCR/RR are numerical analysis techniques for detecting and formulating a mathematical structure (model) within a data set comprising observations associated with multiple objects. Each object has associated with it observations for multiple variables, the latter being common to all objects. These multiple variables are assigned into two categories, known as X-block and Y-block (GC/MS data in this case). Observations associated with all variables in the X-block are realized from a common process. Observations associated with variables in the Y-block (known properties in this case) are realized from processes that may be different for each variable. The data set used to construct this mathematical model is referred to as the model calibration data set.

The common use of PLS/PCR/RR is to apply the model developed from the calibration data set to X-block observations realized for new objects (not in the calibration data set) to predict values for the corresponding variables in the Y-block for these new objects, without having to execute the Y-block processes used in the calibration data set. Using diagnostics that are simultaneously generated by the PLS/PCR/RR model, assessment of whether the new objects can be adequately described by the model, and whether the model is used in an extrapolation mode versus interpolation mode can be performed.

PLS/PCR addresses the collinearity features in the X-block and Y-block, by suitably reducing the dimensionality in both X- and Y-blocks (for PLS), and X-block only (for PCR) to form the model. Collinearity is a term referring to the existence of relationships between variables within the block itself. In the PLS modeling algorithm a number of independent dimensions in the X- and Y-blocks are identified by forming pseudo-variables known as principal components or latent vectors through different sets of linear combinations of original variables in each block. Each set of such combinations constitutes an independent dimension. It comprises a set of coefficients that each value associated with each variable in the block is to be weighted by to arrive at the new value for this dimension. The values for the new, reduced dimensions in the Y-block are regressed onto their counterparts in the new, reduced dimensions of the X-block to arrive at the most parsimonious dimension size (number of latent vectors) and their associated weights, with the final goal of one linear equation generated to permit prediction of Y-block variables using X-block variables. The number of dimensions used to construct the model is determined through optimization of a criterion known as PRESS (Prediction Error Sum of Squares), cumulated by a Cross Validation (CV) technique using the training data set, and, following the general model parsimony principle.

For PCR, the number of independent dimensions in the X-block are first selected and identified in a similar fashion as in PLS by forming principal components. Then, for each variable in the Y-block, a model is obtained by performing ordinary multiple linear regression using the Principal Components as "Prediction Variables".

For Ridge Regression, the collinearity problem is dealt with in a different manner than PLS/PCR. Here a diagonal matrix known as the Lambda Matrix is added to the Covariance Matrix of the X-block with the net effect of stabilizing the numerical computation needed to obtain the model coefficients. The selection of Lambda values is through optimization of PRESS criterion using cross validation of the training set.

Thus, the Chemist's Rule data for the various reference samples derived from GC/MS analysis form the X-block variables. PLS/PCR/RR treatment may require preliminary reorganization of the X-block data, such as transposition and removal of redundant data and constants or mathematical transformations. The Y-block variables are the property (or properties) to be predicted, and may also require mathematical transformations such as logarithmic or geometric, as well as reorganization. The data blocks may be represented by:

X-BLOCK MATRIX
[Chemist's Rules ($n$ samples × 178 columns)]

$$\begin{vmatrix} X_{1,1} & X_{1,2} & X_{1,3} & \ldots & X_{1,176} & X_{1,177} & X_{1,178} \\ X_{2,1} & X_{2,2} & X_{2,3} & \ldots & X_{2,176} & X_{2,177} & X_{2,178} \\ X_{3,1} & X_{3,2} & X_{3,3} & \ldots & X_{3,176} & X_{3,177} & X_{3,178} \\ . & . & . & \ldots & . & . & . \\ . & . & . & \ldots & . & . & . \\ . & . & . & \ldots & . & . & . \\ X_{n,1} & X_{n,2} & X_{n,3} & \ldots & X_{n,176} & X_{n,177} & X_{n,178} \end{vmatrix}$$

Y-BLOCK VECTOR
[Measured property or properties ($n$ samples)]

$$\begin{vmatrix} Y_1 \\ Y_2 \\ Y_3 \\ . \\ . \\ . \\ Y_n \end{vmatrix}$$

The Y-block may be a single observation per set of Chemist's Rules as shown above, or it may be a n×m matrix of observations where there are m different properties to be predicted.

The results of PLS treatment of the training set data are a series of coefficients. Raw GC/MS data from an unknown sample (or samples) are then treated by the Chemist's Rules first to correct the retention times and then to form the ion summations. Each value for the Chemist's Rule ion summation result is then multiplied by the training set coefficients and summed to generate the prediction of the desired property. Table 5 illustrates the quality of the predicted density values for both the training set and the unknown test set for density at 15° C.

TABLE 5

Predicted vs. Measured Waxy Raffinate Density Values @ 15° C. (g/ml)

| | Measured* | Predicted |
|---|---|---|
| | Training Set | |
| 1 | 0.8478 | 0.8481 |
| 2 | 0.8597 | 0.8608 |
| 3 | 0.8642 | 0.8649 |
| 4 | 0.8614 | 0.8645 |
| 5 | 0.8657 | 0.8690 |
| 6 | 0.8616 | 0.8610 |
| 7 | 0.8680 | 0.8665 |
| 8 | 0.8596 | 0.8593 |
| 9 | 0.8596 | 0.8609 |
| 10 | 0.8640 | 0.8637 |
| 11 | 0.8645 | 0.8661 |

TABLE 5-continued

Predicted vs. Measured Waxy Raffinate Density Values @ 15° C. (g/ml)

| | Measured* | Predicted |
|---|---|---|
| | Training Set | |
| 12 | 0.8762 | 0.8772 |
| 13 | 0.8849 | 0.8863 |
| 14 | 0.8607 | 0.8589 |
| 15 | 0.8675 | 0.8652 |
| 16 | 0.8622 | 0.8635 |
| 17 | 0.8699 | 0.8691 |
| 18 | 0.8749 | 0.8743 |
| 19 | 0.8636 | 0.8636 |
| 20 | 0.8636 | 0.8632 |
| 21 | 0.8794 | 0.8771 |
| 22 | 0.8724 | 0.8722 |
| 23 | 0.8600 | 0.8613 |
| | Test Set | |
| 24 | 0.8695 | 0.8691 |
| 25 | 0 8664 | 0.8644 |
| 26 | 0.8665 | 0.8645 |
| 27 | 0.8768 | 0.8758 |

*measured by ASTM D 4052-91

EXAMPLE 2

The procedure of Example 1 was repeated for predicting refractive index @75° C. for the suite of 150N grade waxy raffinates. The same 22 samples were used for the training set, while the remaining five samples were used as a test set. The results for the refractive index at 75° C. are summarized in Table 6.

TABLE 6

Predicted vs. Measured Refractive Index @ 75° C.

| | Measured* | Predicted |
|---|---|---|
| | Training Set | |
| 1 | 1.4441 | 1.4434 |
| 2 | 1.4505 | 1.4504 |
| 3 | 1.4534 | 1.4527 |
| 4 | 1.4509 | 1.4526 |
| 5 | 1.4540 | 1.4551 |
| 6 | 1.4509 | 1.4507 |
| 7 | 1.4550 | 1.4540 |
| 8 | 1.4504 | 1.4499 |
| 9 | 1.4495 | 1.4500 |
| 10 | 1.4523 | 1.4514 |
| 11 | 1.4525 | 1.4532 |
| 12 | 1.4573 | 1.4577 |
| 13 | 1.4628 | 1.4626 |
| 14 | 1.4506 | 1.4500 |
| 15 | 1.4542 | 1.4535 |
| 16 | 1.4528 | 1.4538 |
| 17 | 1.4575 | 1.4571 |
| 18 | 1.4581 | 1.4575 |
| 19 | 1.4505 | 1.4519 |
| 20 | 1.4512 | 1.4519 |
| 21 | 1.4616 | 1.4609 |
| 22 | 1.4576 | 1.4582 |
| | Test Set | |
| 23 | 1.4497 | 1.4503 |
| 24 | 1.4546 | 1.4546 |
| 25 | 1.4525 | 1.4522 |
| 26 | 1.4530 | 1.4526 |
| 27 | 1.4582 | 1.4579 |

*measured by ASTM D 1218-92

EXAMPLE 3

The procedure of Example 1 was repeated for predicting viscosity at 100° C. for 150N grade waxy raffinates. The same 22 samples were used for the training set, while the remaining five samples were used as a test set. The results for density prediction are summarized in Table 7.

TABLE 7

Predicted vs. Measured Viscosity @ 100° C. (cSt)

| | Measured* | Predicted |
|---|---|---|
| | Training Set | |
| 1 | 5.38 | 5.37 |
| 2 | 4.72 | 4.74 |
| 3 | 4.79 | 4.79 |
| 4 | 4.68 | 4.74 |
| 5 | 4.74 | 4.79 |
| 6 | 4.48 | 4.48 |
| 7 | 4.49 | 4.42 |
| 8 | 4.35 | 4.27 |
| 9 | 4.38 | 4.34 |
| 10 | 4.44 | 4.38 |
| 11 | 4.41 | 4.53 |
| 12 | 4.61 | 4.66 |
| 13 | 4.76 | 4.84 |
| 14 | 4.49 | 4.45 |
| 15 | 4.59 | 4.56 |
| 16 | 4.84 | 4.88 |
| 17 | 4.96 | 5.00 |
| 18 | 4.74 | 4.62 |
| 19 | 4.16 | 4.39 |
| 20 | 4.91 | 4.88 |
| 21 | 5.19 | 5.14 |
| | Test Set | |
| 22 | 5.07 | 5.07 |
| 23 | 4.35 | 4.45 |
| 24 | 4.67 | 4.51 |
| 25 | 4.39 | 4.41 |
| 26 | 5.00 | 4.90 |
| 27 | 4.81 | 4.79 |

*measured by ASTM D 445-88

EXAMPLE 4

The procedure of Example 1 was repeated for predicting weight percent wax content for 150N grade waxy raffinates. The same 22 samples were used for the training set, while the remaining five samples were used as a test set. The results for density prediction are summarized in Table 8.

TABLE 8

Predicted vs. Measured Wax Content (Wt %)

| | Measured* | Predicted |
|---|---|---|
| | Training Set | |
| 1 | 21.8 | 22.0 |
| 2 | 25.7 | 23.5 |
| 3 | 20.0 | 21.5 |
| 4 | 20.6 | 20.0 |
| 5 | 19.1 | 17.8 |
| 6 | 29.6 | 29.5 |
| 7 | 17.5 | 18.6 |
| 8 | 20.0 | 21.4 |
| 9 | 20.8 | 19.9 |
| 10 | 19.4 | 18.8 |
| 11 | 18.8 | 19.8 |
| 12 | 3.6 | 3.6 |
| 13 | 2.4 | 0.9 |
| 14 | 18.4 | 20.8 |

TABLE 8-continued

Predicted vs. Measured Wax Content (Wt %)

| | Measured* | Predicted |
|---|---|---|
| 15 | 16.9 | 18.0 |
| 16 | 16.2 | 16.5 |
| 17 | 14.6 | 14.4 |
| 18 | 6.7 | 7.5 |
| 19 | 20.2 | 17.4 |
| 20 | 21.2 | 21.1 |
| Test Set | | |
| 21 | 10.4 | 10.4 |
| 22 | 11.6 | 12.3 |
| 23 | 23.5 | 22.5 |
| 24 | 7.6 | 9.4 |
| 25 | 18.1 | 17.5 |
| 26 | 20.4 | 20.2 |
| 27 | 8.6 | 8.4 |

*measured by ASTM D 3235-88

Other properties of various grades of lubricating intermediate streams or finished products, such as, cloud point, flash point, viscosity index, pour point, basic nitrogen content, distillation and volatility characteristics, viscosity at 40° C., aniline point, sulfur content, etc., could be predicted using the method according to the invention.

The subject method can also be applied for predicting properties of other types of complex hydrocarbon mixtures in similar boiling ranges, such as catalytic cracker feedstock quality, feed to extraction or dewaxing units, feedstocks to distillation or stripping towers, and to blending considerations.

COMPLETE CHEMST'S RULES FOR LUBES

| Rule[a] | Material[b] | Masses[c] | | | | | | Retention Time[d] Starting | Ending |
|---|---|---|---|---|---|---|---|---|---|
| 1 | C16 | 43 | 57 | 71 | 85 | 99 | 113 | 1.00 | 1.89 |
| 2 | ½ Ring | 69 | 83 | 97 | 109 | 123 | 137 | 1.00 | 2.30 |
| 3 | ¾ Ring | 149 | 163 | 177 | 189 | 203 | 217 | 1.00 | 2.30 |
| 4 | ⅘ Ring | 229 | 243 | 257 | 269 | 283 | 297 | 1.00 | 2.30 |
| 5 | 6 Ring | 309 | 223 | 337 | | | | 1.00 | 2.30 |
| 6 | −6 | 91 | 105 | 119 | 133 | 147 | 161 | 1.00 | 2.30 |
| 7 | −6.1 | 92 | 106 | 120 | 134 | 148 | 162 | 1.00 | 2.30 |
| 8 | −8/−10 | 115 | 117 | 129 | 131 | 143 | 145 | 1.00 | 2.30 |
| 9 | −12 | 128 | 141 | 142 | 155 | 156 | 169 | 1.00 | 2.30 |
| 10 | −14/−16 | 151 | 153 | 165 | 167 | 179 | 181 | 1.00 | 2.30 |
| 11 | −18 | 178 | 191 | 192 | 205 | 206 | 219 | 1.00 | 2.30 |
| 12 | −20 | 202 | 215 | 226 | 239 | 228 | 241 | 1.00 | 2.30 |
| 13 | C17 | 43 | 57 | 71 | 85 | 99 | 113 | 1.89 | 1.98 |
| 14 | isoPara | 43 | 57 | 71 | 85 | 99 | 113 | 1.98 | 2.30 |
| 15 | C18 | 43 | 57 | 71 | 85 | 99 | 113 | 2.30 | 2.40 |
| 16 | isoPara | 43 | 57 | 71 | 85 | 99 | 113 | 2.40 | 3.22 |
| 17 | ½ Ring | 69 | 83 | 97 | 109 | 123 | 137 | 2.40 | 3.22 |
| 18 | ¾ Ring | 149 | 163 | 177 | 189 | 203 | 217 | 2.40 | 3.22 |
| 19 | ⅘ Ring | 229 | 243 | 257 | 269 | 283 | 297 | 2.40 | 3.22 |
| 20 | 6 Ring | 309 | 223 | 337 | | | | 2.40 | 3.22 |
| 21 | −6 | 91 | 105 | 119 | 133 | 147 | 161 | 2.40 | 3.22 |
| 22 | −6.1 | 92 | 106 | 120 | 134 | 148 | 162 | 2.40 | 3.22 |
| 23 | −8/−10 | 115 | 117 | 120 | 131 | 143 | 144 | 2.40 | 3.22 |
| 24 | −12 | 128 | 141 | 142 | 155 | 156 | 169 | 2.40 | 3.22 |
| 25 | −14/−16 | 151 | 155 | 165 | 167 | 179 | 181 | 2.40 | 3.22 |
| 26 | −18 | 178 | 191 | 192 | 205 | 206 | 219 | 2.40 | 3.22 |
| 27 | nC19 | 43 | 57 | 71 | 85 | 99 | 113 | 2.70 | 2.85 |
| 28 | isoPara | 43 | 57 | 71 | 85 | 99 | 113 | 2.85 | 3.22 |
| 29 | nC20 | 43 | 57 | 71 | 85 | 99 | 113 | 3.22 | 3.34 |
| 30 | isoPara | 43 | 57 | 71 | 85 | 99 | 113 | 3.34 | 3.70 |
| 31 | ½ Ring | 69 | 83 | 97 | 109 | 123 | 137 | 3.34 | 4.20 |
| 32 | ¾ Ring | 149 | 163 | 177 | 189 | 203 | 217 | 3.34 | 4.20 |
| 33 | ⅘ Ring | 229 | 243 | 257 | 269 | 283 | 297 | 3.34 | 4.20 |
| 34 | 6 Ring | 309 | 223 | 337 | | | | 3.34 | 4.20 |
| 35 | −6 | 91 | 105 | 119 | 133 | 147 | 161 | 3.34 | 4.20 |
| 36 | −6.1 | 92 | 106 | 120 | 134 | 148 | 162 | 3.34 | 4.20 |
| 37 | −8/−10 | 115 | 117 | 129 | 131 | 143 | 145 | 3.34 | 4.20 |
| 38 | −12 | 128 | 141 | 142 | 155 | 156 | 169 | 3.34 | 4.20 |
| 39 | −14/−16 | 151 | 153 | 165 | 167 | 179 | 181 | 3.34 | 4.20 |
| 40 | −18 | 178 | 191 | 192 | 205 | 206 | 219 | 3.34 | 4.20 |
| 41 | −20 | 202 | 215 | 226 | 239 | 228 | 241 | 3.34 | 4.20 |
| 42 | nC21 | 43 | 57 | 71 | 85 | 99 | 113 | 3.70 | 3.83 |
| 43 | isoPara | 43 | 57 | 71 | 85 | 99 | 113 | 3.84 | 4.20 |
| 44 | nC22 | 43 | 57 | 71 | 85 | 99 | 113 | 4.20 | 4.33 |
| 45 | isoPara | 43 | 57 | 71 | 85 | 99 | 113 | 4.33 | 4.72 |
| 46 | ½ Ring | 69 | 83 | 97 | 109 | 123 | 137 | 4.33 | 5.20 |
| 47 | ¾ Ring | 149 | 163 | 177 | 189 | 203 | 217 | 4.33 | 5.20 |
| 48 | ⅘ Ring | 229 | 243 | 257 | 266 | 283 | 297 | 4.33 | 5.20 |
| 49 | 6 Ring | 309 | 223 | 337 | | | | 4.33 | 5.20 |
| 50 | −6 | 91 | 105 | 119 | 133 | 147 | 161 | 4.33 | 5.20 |
| 51 | −6.1 | 92 | 106 | 120 | 134 | 148 | 162 | 4.33 | 5.20 |
| 52 | −8/−10 | 115 | 117 | 129 | 131 | 143 | 145 | 4.33 | 5.20 |
| 53 | −12 | 128 | 141 | 142 | 155 | 156 | 169 | 4.33 | 5.20 |
| 54 | −14/−16 | 151 | 153 | 165 | 167 | 179 | 181 | 4.33 | 5.20 |
| 55 | −18 | 178 | 191 | 192 | 205 | 206 | 219 | 4.33 | 5.20 |
| 56 | −20 | 202 | 215 | 226 | 239 | 228 | 241 | 4.33 | 5.20 |
| 57 | C23 | 43 | 57 | 71 | 85 | 99 | 113 | 4.72 | 4.83 |
| 58 | isoPara | 43 | 57 | 71 | 85 | 99 | 113 | 4.83 | 5.20 |
| 59 | nC24 | 43 | 57 | 71 | 85 | 99 | 113 | 5.20 | 5.37 |
| 60 | isoPara | 43 | 57 | 71 | 85 | 99 | 113 | 5.38 | 5.64 |
| 61 | ½ Ring | 69 | 83 | 97 | 109 | 123 | 137 | 5.38 | 6.15 |
| 62 | ¾ Ring | 149 | 163 | 177 | 189 | 203 | 217 | 5.38 | 6.15 |
| 63 | ⅘ Ring | 229 | 243 | 257 | 269 | 283 | 297 | 5.38 | 6.15 |
| 64 | 6 Ring | 309 | 223 | 337 | | | | 5.38 | 6.15 |
| 65 | −6 | 91 | 105 | 119 | 133 | 147 | 161 | 5.38 | 6.15 |
| 66 | −6.1 | 92 | 106 | 120 | 134 | 148 | 162 | 5.38 | 6.15 |
| 67 | −8/−10 | 115 | 117 | 129 | 131 | 143 | 145 | 5.38 | 6.15 |
| 68 | −12 | 128 | 141 | 142 | 155 | 156 | 169 | 5.38 | 6.15 |
| 69 | −14/−16 | 151 | 153 | 165 | 167 | 179 | 181 | 5.38 | 6.15 |
| 70 | −18 | 178 | 191 | 192 | 205 | 206 | 219 | 5.38 | 6.15 |
| 71 | −20 | 202 | 215 | 226 | 239 | 228 | 241 | 5.38 | 6.15 |
| 72 | nC25 | 43 | 57 | 71 | 85 | 99 | 113 | 5.65 | 5.85 |
| 73 | isoPara | 43 | 57 | 71 | 85 | 99 | 113 | 5.85 | 6.15 |
| 74 | C26 | 43 | 57 | 71 | 85 | 99 | 113 | 6.15 | 6.32 |
| 75 | isoPara | 43 | 57 | 71 | 85 | 99 | 113 | 6.33 | 6.64 |
| 76 | ½ Ring | 69 | 83 | 97 | 109 | 123 | 137 | 6.33 | 7.04 |
| 77 | ¾ Ring | 149 | 163 | 177 | 189 | 203 | 217 | 6.33 | 7.04 |
| 78 | ⅘ Ring | 229 | 243 | 257 | 269 | 283 | 297 | 6.33 | 7.04 |
| 79 | 6 Ring | 309 | 223 | 337 | | | | 6.33 | 7.04 |
| 80 | −6 | 91 | 105 | 119 | 133 | 147 | 161 | 6.33 | 7.04 |
| 81 | −6.1 | 92 | 106 | 120 | 134 | 148 | 162 | 6.33 | 7.04 |
| 82 | −8/−10 | 115 | 117 | 129 | 131 | 143 | 145 | 6.33 | 7.04 |
| 83 | −12 | 128 | 141 | 142 | 155 | 156 | 169 | 6.33 | 7.04 |
| 84 | −14/−16 | 151 | 153 | 165 | 167 | 179 | 181 | 6.33 | 7.04 |
| 85 | −18 | 178 | 191 | 192 | 205 | 206 | 219 | 6.33 | 7.04 |
| 86 | −20 | 202 | 215 | 226 | 239 | 228 | 241 | 6.33 | 7.04 |
| 87 | nC27 | 43 | 57 | 71 | 85 | 99 | 113 | 6.65 | 6.75 |
| 88 | isoPara | 43 | 57 | 71 | 85 | 99 | 113 | 6.76 | 7.04 |
| 89 | nC28 | 43 | 57 | 71 | 85 | 99 | 113 | 7.05 | 7.20 |
| 90 | isoPara | 43 | 57 | 71 | 85 | 99 | 113 | 7.21 | 7.45 |
| 91 | 1/2 Rin | 69 | 83 | 97 | 109 | 123 | 137 | 7.21 | 7.85 |
| 92 | ¾ Ring | 149 | 163 | 177 | 189 | 203 | 217 | 7.21 | 7.85 |
| 93 | ⅘ Ring | 229 | 243 | 257 | 269 | 283 | 297 | 7.21 | 7.85 |
| 94 | 6 Ring | 309 | 223 | 337 | | | | 7.21 | 7.85 |
| 95 | −6 | 91 | 105 | 119 | 133 | 147 | 161 | 7.21 | 7.85 |
| 96 | −6.1 | 92 | 106 | 120 | 134 | 148 | 162 | 7.21 | 7.85 |
| 97 | −8/−10 | 115 | 117 | 129 | 131 | 143 | 145 | 7.21 | 7.85 |
| 98 | −12 | 128 | 141 | 142 | 155 | 156 | 169 | 7.21 | 7.85 |
| 99 | −14/−16 | 151 | 153 | 165 | 167 | 179 | 181 | 7.21 | 7.85 |
| 100 | −18 | 178 | 191 | 192 | 205 | 206 | 219 | 7.21 | 7.85 |
| 101 | −20 | 202 | 215 | 226 | 239 | 228 | 241 | 7.21 | 7.85 |
| 102 | nC29 | 43 | 57 | 71 | 85 | 99 | 113 | 7.46 | 7.65 |
| 103 | isoPara | 43 | 57 | 71 | 85 | 99 | 113 | 7.66 | 7.85 |

COMPLETE CHEMIST'S RULES FOR LUBES

| Rule[a] | Material[b] | Masses[c] | | | | | | Retention Time[d] Starting | Ending |
|---|---|---|---|---|---|---|---|---|---|
| 104 | nC30 | 43 | 57 | 71 | 85 | 99 | 113 | 7.85 | 8.00 |
| 105 | isoPara | 43 | 57 | 71 | 85 | 99 | 113 | 8.01 | 8.30 |
| 106 | ½ Ring | 69 | 83 | 97 | 109 | 123 | 137 | 8.01 | 8.65 |
| 107 | ¾ Ring | 149 | 163 | 177 | 189 | 203 | 217 | 8.01 | 8.65 |
| 108 | ⅘ Ring | 229 | 243 | 257 | 269 | 283 | 297 | 8.01 | 8.65 |
| 109 | 6 Ring | 309 | 223 | 337 | | | | 8.01 | 8.65 |
| 110 | -6 | 91 | 105 | 119 | 133 | 147 | 161 | 8.01 | 8.65 |
| 111 | -6.1 | 92 | 106 | 120 | 134 | 148 | 162 | 8.01 | 8.65 |
| 112 | -8/-10 | 115 | 117 | 129 | 131 | 143 | 145 | 8.01 | 8.65 |
| 113 | -12 | 128 | 141 | 142 | 155 | 156 | 169 | 8.01 | 8.65 |
| 114 | -14/-16 | 151 | 153 | 165 | 167 | 179 | 181 | 8.01 | 8.65 |
| 115 | -18 | 178 | 191 | 192 | 205 | 206 | 219 | 8.01 | 8.65 |
| 116 | -20 | 202 | 215 | 226 | 239 | 228 | 241 | 8.01 | 8.25 |
| 117 | nC31 | 43 | 57 | 71 | 85 | 99 | 113 | 8.38 | 8.37 |
| 118 | isoPara | 43 | 57 | 71 | 85 | 99 | 113 | 8.38 | 8.65 |
| 119 | nC32 | 43 | 57 | 71 | 85 | 99 | 113 | 8.68 | 8.79 |
| 120 | isoPara | 43 | 57 | 71 | 85 | 99 | 113 | 8.77 | 8.99 |
| 121 | ½ Ring | 69 | 83 | 97 | 109 | 123 | 137 | 8.77 | 9.45 |
| 122 | ¾ Ring | 149 | 163 | 177 | 189 | 203 | 217 | 8.77 | 9.45 |
| 123 | ⅘ Ring | 229 | 243 | 257 | 269 | 283 | 297 | 8.77 | 9.45 |
| 124 | 6 Ring | 309 | 223 | 337 | | | | 8.77 | 9.45 |
| 125 | -6 | 91 | 105 | 119 | 133 | 147 | 161 | 8.77 | 9.45 |
| 126 | -6.1 | 92 | 106 | 120 | 134 | 148 | 162 | 8.77 | 9.45 |
| 127 | -8/-10 | 115 | 117 | 129 | 131 | 143 | 145 | 8.77 | 9.45 |
| 128 | -12 | 128 | 141 | 142 | 155 | 156 | 169 | 8.77 | 9.45 |
| 129 | -14/-16 | 151 | 153 | 165 | 167 | 179 | 181 | 8.77 | 9.45 |
| 130 | -18 | 178 | 191 | 192 | 205 | 206 | 219 | 8.77 | 9.45 |
| 131 | -20 | 202 | 215 | 226 | 239 | 228 | 241 | 8.77 | 9.45 |
| 132 | nC33 | 43 | 57 | 71 | 85 | 99 | 113 | 8.95 | 9.11 |
| 133 | isoPara | 43 | 57 | 71 | 85 | 99 | 113 | 9.11 | 9.50 |
| 134 | nC34 | 43 | 57 | 71 | 85 | 95 | 113 | 9.50 | 9.56 |
| 135 | isoPara | 43 | 57 | 71 | 85 | 99 | 113 | 9.56 | 9.92 |
| 136 | ½ Ring | 69 | 83 | 97 | 109 | 123 | 113 | 9.56 | 10.51 |
| 137 | ¾ Ring | 149 | 163 | 177 | 189 | 203 | 217 | 9.56 | 10.51 |
| 138 | ⅘ Ring | 229 | 243 | 257 | 269 | 283 | 297 | 9.56 | 10.51 |
| 139 | 6 Ring | 309 | 223 | 337 | | | | 9.56 | 10.51 |
| 140 | -6 | 91 | 105 | 119 | 133 | 147 | 161 | 9.56 | 10.51 |
| 141 | -6.1 | 92 | 106 | 120 | 134 | 148 | 162 | 9.56 | 10.51 |
| 142 | -8/-10 | 115 | 117 | 129 | 131 | 143 | 145 | 9.56 | 10.51 |
| 143 | -12 | 128 | 141 | 142 | 155 | 156 | 169 | 9.56 | 10.51 |
| 144 | -14/-16 | 151 | 153 | 165 | 167 | 179 | 181 | 9.56 | 10.51 |
| 145 | -18 | 178 | 191 | 192 | 205 | 206 | 219 | 9.56 | 10.51 |
| 146 | -20 | 202 | 215 | 226 | 239 | 228 | 241 | 9.56 | 10.51 |
| 147 | nC35 | 43 | 57 | 71 | 85 | 99 | 113 | 9.93 | 10.04 |
| 148 | isoPara | 43 | 57 | 71 | 85 | 99 | 113 | 10.04 | 10.51 |
| 149 | nC36 | 43 | 57 | 71 | 85 | 99 | 113 | 10.51 | 10.67 |
| 150 | isoPara | 43 | 57 | 71 | 85 | 99 | 113 | 10.67 | 11.16 |
| 151 | ½ Ring | 69 | 83 | 97 | 109 | 123 | 137 | 10.67 | 11.93 |
| 152 | ¾ Ring | 149 | 163 | 177 | 189 | 203 | 217 | 10.67 | 11.93 |
| 153 | ⅘ Ring | 229 | 243 | 257 | 269 | 288 | 297 | 10.67 | 11.93 |
| 154 | 6 Ring | 309 | 223 | 337 | | | | 10.67 | 11.93 |
| 155 | -6 | 91 | 105 | 119 | 133 | 147 | 161 | 10.67 | 11.93 |
| 156 | -6.1 | 92 | 105 | 120 | 134 | 148 | 162 | 10.67 | 11.93 |
| 157 | -8/-10 | 115 | 117 | 129 | 131 | 143 | 145 | 10.67 | 11.93 |
| 158 | 12 | 128 | 141 | 142 | 155 | 156 | 169 | 10.67 | 11.93 |
| 159 | -14/-16 | 151 | 153 | 165 | 167 | 179 | 181 | 10.67 | 11.93 |
| 160 | -18 | 178 | 191 | 192 | 205 | 206 | 219 | 10.67 | 11.93 |
| 161 | -20 | 202 | 215 | 226 | 239 | 228 | 241 | 10.67 | 11.93 |
| 162 | nC37 | 43 | 57 | 71 | 85 | 99 | 113 | 11.17 | 11.28 |
| 163 | isoPara | 43 | 57 | 71 | 85 | 99 | 113 | 11.2 | 11.93 |
| 164 | nC38 | 43 | 57 | 71 | 85 | 99 | 113 | 11.9 | 12.06 |
| 165 | isoPara | 43 | 57 | 71 | 85 | 99 | 113 | 12.07 | 12.83 |
| 166 | ½ Ring | 69 | 83 | 97 | 109 | 123 | 137 | 12.07 | 14.00 |
| 167 | ¾ Ring | 149 | 163 | 177 | 189 | 203 | 217 | 12.07 | 14.00 |
| 168 | ⅘ Ring | 229 | 243 | 255 | 269 | 283 | 297 | 12.07 | 14.00 |
| 169 | 6 Ring | 309 | 223 | 337 | | | | 12.07 | 14.00 |
| 170 | -6 | 91 | 105 | 119 | 133 | 147 | 161 | 12.07 | 14.00 |
| 171 | -6.1 | 92 | 106 | 120 | 134 | 148 | 162 | 12.07 | 14.00 |
| 172 | -8/-10 | 115 | 117 | 129 | 131 | 143 | 145 | 12.07 | 14.00 |
| 173 | -12 | 128 | 141 | 142 | 155 | 156 | 169 | 12.07 | 14.00 |
| 174 | -14/-16 | 151 | 153 | 165 | 167 | 179 | 181 | 12.07 | 14.00 |
| 175 | -18 | 178 | 191 | 192 | 205 | 206 | 219 | 12.07 | 14.00 |
| 176 | -20 | 202 | 215 | 226 | 239 | 228 | 241 | 12.07 | 14.00 |
| 177 | nC39 | 43 | 57 | 71 | 85 | 99 | 113 | 12.83 | 12.87 |
| 178 | isoPara | 43 | 57 | 71 | 85 | 99 | 113 | 12.83 | 14.00 |

[a]Rule number, integer index
[b]Compound or group of compound rule applies to:
½ ring   ½ ring cycloparaffins
¾ ring   ¾ ring cycloparaffins
⅘ ring   ⅘ ring cycloparaffins
6 ring   6 ring cycloparaffins
-6       $C_nH_{2n-6}$ alkylated benzenes
-6.1     $C_nH_{2n-6}$ LINEAR alkylated benzenes
-8/-10   $C_nH_{2n-8}$ alkylated indanes, $C_nH_{2n-10}$ alkylated indenes
-12      $C_nH_{2n-12}$ alkylated naphthalenes
-14/16   $C_nH_{2n-14}$ alkylated acenaphthenes/$C_nH_{2n-16}$ alkylated acenaphthalenes
-18      $C_nH_{2n-18}$ alkylated phenanthrenes/anthracenes
-20      $C_nH_{2n-20}$ alkylated naphthenophenanthrenes

[c]Masses used in Rule [up to n may be specified, wherein is an integer which is equal to the number of masses scanned during the time interval (d)].
[d]Retention time for both starting and ending expected retention times based on historical averages in minutes.

COMPLETE CHEMIST'S RULES FOR LUBES

Total Raw Abundance (TIC): 770247450
Chemist Rule: 398341548   -51.72%
Air Leakage: 247241   -0.03%
Avg Scan Rate (Min/Max): 292   (292/293)
Number of Records: 2864

| Rule[a] | Compound[b] | Masses[c] | | | | | | Start[d] | End[e] | CStart[f] | Corr[g] | CEnd[h] | Corr[i] | Abundance[j] | |
|---|---|---|---|---|---|---|---|---|---|---|---|---|---|---|---|
| 1 | nC16 | 43 | 57 | 71 | 85 | 99 | 113 | 1.000 | 1.890 | 0.998 | -0.002 | 1.886 | -0.004 | 11823 | 0.00% |
| 2 | ½ Ring | 69 | 83 | 97 | 109 | 123 | 137 | 1.000 | 2.300 | 0.998 | -0.002 | 2.295 | -0.005 | 32274 | 0.01% |
| 3 | ¾ Ring | 149 | 163 | 177 | 189 | 203 | 217 | 1.000 | 2.300 | 0.998 | -0.002 | 2.295 | -0.005 | 0 | 0.00% |
| 4 | ⅘ Ring | 229 | 243 | 257 | 269 | 283 | 297 | 1.000 | 2.300 | 0.998 | -0.002 | 2.295 | -0.005 | 0 | 0.00% |

-continued

COMPLETE CHEMIST'S RULES FOR LUBES

Total Raw Abundance (TIC): 770247450  
Chemist Rule: 398341548 −51.72%  
Air Leakage: 247241 −0.03%  
Avg Scan Rate (Min/Max): 292 (292/293)  
Number of Records: 2864

| Rule[a] | Compound[b] | Masses[c] | | | | | | Start[d] | End[e] | CStart[f] | Corr[g] | CEnd[h] | Corr[i] | Abundance[j] | |
|---|---|---|---|---|---|---|---|---|---|---|---|---|---|---|---|
| 5 | 6 Ring | 309 | 223 | 337 | | | | 1.000 | 2.300 | 0.998 | −0.002 | 2.295 | −0.005 | 0 | 0.00% |
| 6 | −6 | 91 | 105 | 119 | 133 | 147 | 161 | 1.000 | 2.300 | 0.998 | −0.002 | 2.295 | −0.005 | 0 | 0.00% |
| 7 | −6.1 | 92 | 106 | 120 | 134 | 148 | 162 | 1.000 | 2.300 | 0.998 | −0.002 | 2.295 | −0.005 | 0 | 0.00% |
| 8 | −8/−10 | 115 | 117 | 129 | 131 | 143 | 145 | 1.000 | 2.300 | 0.998 | −0.002 | 2.295 | −0.005 | 0 | 0.00% |
| 9 | −12 | 128 | 141 | 142 | 155 | 156 | 169 | 1.000 | 2.300 | 0.998 | −0.002 | 2.295 | −0.005 | 0 | 0.00% |
| 10 | −14/−16 | 151 | 153 | 165 | 167 | 179 | 181 | 1.000 | 2.300 | 0.998 | −0.002 | 2.295 | −0.005 | 0 | 0.00% |
| 11 | −18 | 178 | 191 | 192 | 205 | 206 | 219 | 1.000 | 2.300 | 0.998 | −0.002 | 2.295 | −0.005 | 0 | 0.00% |
| 12 | −20 | 202 | 215 | 226 | 239 | 228 | 241 | 1.000 | 2.300 | 0.998 | −0.002 | 2.295 | −0.005 | 0 | 0.00% |
| 13 | nC17 | 43 | 57 | 71 | 85 | 99 | 113 | 1.890 | 1.980 | 1.886 | −0.004 | 1.976 | −0.004 | 83071 | 0.02% |
| 14 | isoPara | 43 | 57 | 71 | 85 | 99 | 113 | 1.980 | 2.300 | 1.976 | −0.004 | 2.295 | −0.005 | 163356 | 0.04% |
| 15 | nC18 | 43 | 57 | 71 | 85 | 99 | 113 | 2.300 | 2.400 | 2.295 | −0.005 | 2.395 | −0.005 | 417625 | 0.11% |
| 16 | isoPara | 43 | 57 | 71 | 85 | 99 | 113 | 2.400 | 3.220 | 2.395 | −0.005 | 3.216 | −0.004 | 3447651 | 0.87% |
| 17 | ½ Ring | 69 | 83 | 97 | 109 | 123 | 137 | 2.400 | 3.220 | 2.395 | −0.005 | 3.216 | −0.004 | 1770916 | 0.45% |
| 18 | ¾ Ring | 149 | 163 | 177 | 189 | 203 | 217 | 2.400 | 3.220 | 2.395 | −0.005 | 3.216 | −0.004 | 1689 | 0.00% |
| 19 | ⅘ Ring | 229 | 243 | 257 | 269 | 283 | 297 | 2.400 | 3.220 | 2.395 | −0.005 | 3.216 | −0.004 | 0 | 0.00% |
| 20 | 6Ring | 309 | 223 | 337 | | | | 2.400 | 3.220 | 2.395 | −0.005 | 3.216 | −0.004 | 0 | 0.00% |
| 21 | −6 | 91 | 105 | 119 | 133 | 147 | 161 | 2.400 | 3.220 | 2.395 | −0.005 | 3.216 | −0.004 | 252005 | 0.06% |
| 22 | −6.1 | 92 | 106 | 120 | 134 | 148 | 162 | 2.400 | 3.220 | 2.395 | −0.005 | 3.216 | −0.004 | 40912 | 0.01% |
| 23 | −8/−10 | 115 | 117 | 129 | 131 | 143 | 145 | 2.400 | 3.220 | 2.395 | −0.005 | 3.216 | −0.004 | 23066 | 0.01% |
| 24 | −12 | 128 | 141 | 142 | 155 | 156 | 169 | 2.400 | 3.220 | 2.395 | −0.005 | 3.216 | −0.004 | 101855 | 0.03% |
| 25 | −14/−16 | 151 | 153 | 165 | 167 | 179 | 181 | 2.400 | 3.220 | 2.395 | −0.005 | 3.216 | −0.004 | 66755 | 0.02% |
| 26 | −18 | 178 | 191 | 192 | 205 | 206 | 219 | 2.400 | 3.220 | 2.395 | −0.005 | 3.216 | −0.004 | 0 | 0.00% |
| 27 | nC19 | 43 | 57 | 71 | 85 | 99 | 113 | 2.700 | 2.850 | 2.694 | −0.006 | 2.844 | −0.006 | 1261176 | 0.32% |
| 28 | isoPara | 43 | 57 | 71 | 85 | 99 | 113 | 2.850 | 3.220 | 2.844 | −0.006 | 3.216 | −0.004 | 1569696 | 0.39% |
| 29 | nC20 | 43 | 57 | 71 | 85 | 99 | 113 | 3.220 | 3.340 | 3.216 | −0.004 | 3.336 | −0.004 | 2627313 | 0.66% |
| 30 | isoPara | 43 | 57 | 71 | 85 | 99 | 113 | 3.340 | 3.700 | 3.336 | −0.004 | 3.697 | −0.003 | 3367639 | 0.85% |
| 31 | ½ Ring | 69 | 83 | 97 | 109 | 123 | 137 | 3.340 | 4.200 | 3.336 | −0.004 | 4.199 | −0.001 | 7813782 | 1.96% |
| 32 | ¾ Ring | 149 | 163 | 177 | 189 | 203 | 217 | 3.340 | 4.200 | 3.336 | −0.004 | 4.199 | −0.001 | 414892 | 0.10% |
| 33 | ⅘ Ring | 229 | 243 | 257 | 269 | 283 | 297 | 3.340 | 4.200 | 3.336 | −0.004 | 4.199 | −0.001 | 1895 | 0.00% |
| 34 | 6Ring | 309 | 223 | 337 | | | | 3.340 | 4.200 | 3.336 | −0.004 | 4.199 | −0.001 | 0 | 0.00% |
| 35 | −6 | 91 | 105 | 119 | 133 | 147 | 161 | 3.340 | 4.200 | 3.336 | −0.004 | 4.199 | −0.001 | 1848494 | 0.46% |
| 36 | −6.1 | 92 | 106 | 120 | 134 | 148 | 162 | 3.340 | 4.200 | 3.336 | −0.004 | 4.199 | −0.001 | 862453 | 0.22% |
| 37 | −8/−10 | 115 | 117 | 129 | 131 | 143 | 145 | 3.340 | 4.200 | 3.336 | −0.004 | 4.199 | −0.001 | 1079195 | 0.27% |
| 38 | −12 | 128 | 141 | 142 | 155 | 156 | 169 | 3.340 | 4.200 | 3.336 | −0.004 | 4.199 | −0.001 | 1011467 | 0.25% |
| 39 | −14/−16 | 151 | 153 | 165 | 167 | 179 | 181 | 3.340 | 4.200 | 3.336 | −0.004 | 4.199 | −0.001 | 1035379 | 0.26% |
| 40 | −18 | 178 | 191 | 192 | 205 | 206 | 219 | 3.340 | 4.200 | 3.336 | −0.004 | 4.199 | −0.001 | 76099 | 0.02% |
| 41 | −20 | 202 | 215 | 226 | 239 | 228 | 241 | 3.340 | 4.200 | 3.336 | −0.004 | 4.199 | −0.001 | 35069 | 0.01% |
| 42 | nC21 | 43 | 57 | 71 | 85 | 99 | 113 | 3.700 | 3.830 | 3.697 | −0.003 | 3.828 | −0.002 | 4517562 | 1.13% |
| 43 | isoPara | 43 | 57 | 71 | 85 | 99 | 113 | 3.840 | 4.200 | 3.838 | −0.002 | 4.199 | −0.001 | 5712240 | 1.43% |
| 44 | nC22 | 43 | 57 | 71 | 85 | 99 | 113 | 4.200 | 4.330 | 4.199 | −0.001 | 4.329 | −0.001 | 6538372 | 1.64% |
| 45 | isoPara | 43 | 57 | 71 | 85 | 99 | 113 | 4.330 | 4.720 | 4.329 | −0.001 | 4.720 | 0.001 | 8802970 | 2.21% |
| 46 | ½ Ring | 69 | 83 | 97 | 109 | 123 | 137 | 4.330 | 5.200 | 4.329 | −0.001 | 5.202 | 0.002 | 15952736 | 4.01% |
| 47 | ¾ Ring | 149 | 163 | 177 | 189 | 203 | 217 | 4.330 | 5.200 | 4.329 | −0.001 | 5.202 | 0.002 | 1365128 | 0.34% |
| 48 | ⅘ Ring | 229 | 243 | 257 | 269 | 283 | 297 | 4.330 | 5.200 | 4.329 | −0.001 | 5.202 | 0.002 | 68439 | |
| 49 | 6Ring | 309 | 223 | 337 | | | | 4.330 | 5.200 | 4.329 | −0.001 | 5.202 | 0.002 | 140447 | 0.04% |
| 50 | −6 | 91 | 105 | 119 | 133 | 147 | 161 | 4.330 | 5.200 | 4.329 | −0.001 | 5.202 | 0.002 | 4256883 | 1.07% |
| 51 | −6.1 | 92 | 106 | 120 | 134 | 148 | 162 | 4.330 | 5.200 | 4.329 | −0.001 | 5.202 | 0.002 | 2068280 | 0.52% |
| 52 | −8/−10 | 115 | 117 | 129 | 131 | 143 | 145 | 4.330 | 5.200 | 4.329 | −0.001 | 5.202 | 0.002 | 2528518 | 0.64% |
| 53 | −12 | 128 | 141 | 142 | 155 | 156 | 169 | 4.330 | 5.200 | 4.329 | −0.001 | 5.202 | 0.002 | 2281283 | 0.57% |
| 54 | −14/−16 | 151 | 153 | 165 | 167 | 179 | 181 | 4.330 | 5.200 | 4.329 | −0.001 | 5.202 | 0.002 | 2249950 | 0.57% |
| 55 | −18 | 178 | 191 | 192 | 205 | 206 | 219 | 4.330 | 5.200 | 4.329 | −0.001 | 5.202 | 0.002 | 667279 | 0.17% |
| 56 | −20 | 202 | 215 | 226 | 239 | 228 | 241 | 4.330 | 5.200 | 4.329 | −0.001 | 5.202 | 6.002 | 235422 | 0.06% |
| 57 | nC23 | 43 | 57 | 71 | 85 | 99 | 113 | 4.720 | 4.830 | 4.720 | 0.001 | 4.831 | 0.001 | 7396326 | 1.86% |
| 58 | isoPara | 43 | 57 | 71 | 85 | 99 | 113 | 4.830 | 5.200 | 4.831 | 0.001 | 5.202 | 0.002 | 10384280 | 2.61% |
| 59 | nC24 | 43 | 57 | 71 | 85 | 99 | 113 | 5.200 | 5.370 | 5.202 | 0.002 | 5.373 | 0.003 | 9950399 | 2.50% |
| 60 | isoPara | 43 | 57 | 71 | 85 | 99 | 113 | 5.380 | 5.640 | 5.383 | 0.003 | 5.644 | 0.004 | 8629779 | 2.17% |
| 61 | ½ Ring | 69 | 83 | 97 | 109 | 123 | 137 | 5.380 | 6.150 | 5.383 | 0.003 | 6.155 | 0.005 | 18498014 | 4.64% |
| 62 | ¾ Ring | 149 | 163 | 177 | 189 | 203 | 217 | 5.380 | 6.150 | 5.383 | 0.003 | 6.155 | 0.005 | 1782810 | 0.45% |
| 63 | ⅘ Ring | 229 | 243 | 257 | 269 | 283 | 297 | 5.380 | 6.150 | 5.383 | 0.003 | 6.155 | 0.005 | 423479 | 0.11% |
| 64 | 6Ring | 309 | 223 | 337 | | | | 5.380 | 6.150 | 5.383 | 0.003 | 6.155 | 0.005 | 413658 | 0.10% |
| 65 | −6 | 91 | 105 | 119 | 133 | 147 | 161 | 5.380 | 6.150 | 5.383 | 0.003 | 6.155 | 0.005 | 5310908 | 1.33% |
| 66 | −6.1 | 92 | 106 | 120 | 134 | 148 | 162 | 5.380 | 6.150 | 5.383 | 0.003 | 6.155 | 0.005 | 2736748 | 0.69% |
| 67 | −8/−10 | 115 | 117 | 129 | 131 | 143 | 145 | 5.380 | 6.150 | 5.383 | 0.003 | 6.155 | 0.005 | 3328600 | 0.84% |
| 68 | −12 | 128 | 141 | 142 | 155 | 156 | 169 | 5.380 | 6.150 | 5.383 | 0.003 | 6.155 | 0.005 | 2892689 | 0.73% |
| 69 | −14/−16 | 151 | 153 | 165 | 167 | 179 | 181 | 5.380 | 6.150 | 5.383 | 0.003 | 6.155 | 0.005 | 2890529 | 0.73% |
| 70 | −18 | 178 | 191 | 192 | 205 | 206 | 219 | 5.380 | 6.150 | 5.383 | 0.003 | 6.155 | 0.005 | 974605 | 0.25% |
| 71 | −20 | 202 | 215 | 226 | 239 | 228 | 241 | 5.380 | 6.150 | 5.383 | 0.003 | 6.155 | 0.005 | 512283 | 0.13% |
| 72 | nC25 | 43 | 57 | 71 | 85 | 99 | 113 | 5.650 | 5.850 | 5.654 | 0.004 | 5.854 | 0.004 | 10630114 | 2.67% |
| 73 | isoPara | 43 | 57 | 71 | 85 | 99 | 113 | 5.850 | 6.150 | 5.854 | 0.004 | 6.155 | 0.005 | 10286314 | 2.58% |
| 74 | nC26 | 43 | 57 | 71 | 85 | 99 | 113 | 6.150 | 6.320 | 6.155 | 0.005 | 6.325 | 0.005 | 9537987 | 2.39% |
| 75 | isoPara | 43 | 57 | 71 | 85 | 99 | 113 | 6.330 | 6.640 | 6.335 | 0.005 | 6.644 | 0.004 | 10594028 | 2.66% |

-continued

COMPLETE CHEMIST'S RULES FOR LUBES

Total Raw Abundance (TIC): 770247450
Chemist Rule: 398341548  −51.72%
Air Leakage: 247241  −0.03%
Avg Scan Rate (Min/Max): 292 (292/293)
Number of Records: 2864

| Rule[a] | Compound[b] | Masses[c] | | | | | | Start[d] | End[e] | CStart[f] | Corr[g] | CEnd[h] | Corr[i] | Abundance[j] | |
|---|---|---|---|---|---|---|---|---|---|---|---|---|---|---|---|
| 76 | ½ Ring | 69 | 83 | 97 | 109 | 123 | 137 | 6.330 | 7.040 | 6.335 | 0.005 | 7.043 | 0.003 | 17499504 | 4.39% |
| 77 | ¾ Ring | 149 | 163 | 177 | 189 | 203 | 217 | 6.330 | 7.040 | 6.335 | 0.005 | 7.043 | 0.003 | 2316602 | 0.58% |
| 78 | ⅘ Ring | 229 | 243 | 257 | 269 | 283 | 297 | 6.330 | 7.040 | 6.335 | 0.005 | 7.043 | 0.003 | 580525 | 0.15% |
| 79 | 6Ring | 309 | 223 | 337 | | | | 6.330 | 7.040 | 6.335 | 0.005 | 7.043 | 0.003 | 420572 | 0.11% |
| 80 | −6 | 91 | 105 | 119 | 133 | 147 | 161 | 6.330 | 7.040 | 6.335 | 0.005 | 7.043 | 0.003 | 5186562 | 1.30% |
| 81 | −6.1 | 92 | 106 | 120 | 134 | 148 | 162 | 6.330 | 7.040 | 6.335 | 0.005 | 7.043 | 0.003 | 2312434 | 0.58% |
| 82 | −8/−10 | 115 | 117 | 129 | 131 | 143 | 145 | 6.330 | 7.040 | 6.335 | 0.005 | 7.043 | 0.003 | 3292559 | 0.83% |
| 83 | −12 | 128 | 141 | 142 | 155 | 156 | 169 | 6.330 | 7.040 | 6.335 | 0.005 | 7.043 | 0.003 | 2863369 | 0.72% |
| 84 | −14/−16 | 151 | 153 | 165 | 167 | 179 | 181 | 6.330 | 7.040 | 6.335 | 0.005 | 7.043 | 0.003 | 2968138 | 0.75% |
| 85 | −18 | 178 | 191 | 192 | 205 | 206 | 219 | 6.330 | 7.040 | 6.335 | 0.005 | 7.043 | 0.003 | 1119484 | 0.28% |
| 86 | −20 | 202 | 215 | 226 | 239 | 228 | 241 | 6.330 | 7.040 | 6.335 | 0.005 | 7.043 | 0.003 | 592555 | 0.15% |
| 87 | nC27 | 43 | 57 | 71 | 85 | 99 | 113 | 6.650 | 6.750 | 6.654 | 0.004 | 6.754 | 0.004 | 6392959 | 1.61% |
| 88 | isoPara | 43 | 57 | 71 | 85 | 99 | 113 | 6.760 | 7.040 | 6.764 | 0.004 | 7.043 | 0.003 | 8926838 | 2.24% |
| 89 | nC28 | 43 | 57 | 71 | 85 | 99 | 113 | 7.050 | 7.200 | 7.053 | 0.003 | 7.202 | 0.002 | 6688519 | 1.68% |
| 90 | isoPara | 43 | 57 | 71 | 85 | 99 | 113 | 7.210 | 7.450 | 7.212 | 0.002 | 7.451 | 0.001 | 7022929 | 1.76% |
| 91 | ½ Ring | 69 | 83 | 97 | 109 | 123 | 137 | 7.210 | 7.850 | 7.212 | 0.002 | 7.850 | 0.000 | 14452201 | 3.63% |
| 92 | ¾ Ring | 149 | 163 | 177 | 189 | 203 | 217 | 7.210 | 7.850 | 7.212 | 0.002 | 7.850 | 0.000 | 2704187 | 0.68% |
| 93 | ⅘ Ring | 229 | 243 | 257 | 269 | 283 | 297 | 7.210 | 7.850 | 7.212 | 0.002 | 7.850 | 0.000 | 487096 | 0.12% |
| 94 | 6Ring | 309 | 223 | 337 | | | | 7.210 | 7.850 | 7.212 | 0.002 | 7.850 | 0.000 | 269192 | 0.07% |
| 95 | −6 | 91 | 105 | 119 | 133 | 147 | 161 | 7.210 | 7.850 | 7.212 | 0.002 | 7.850 | 0.000 | 4363748 | 1.10% |
| 96 | −6.1 | 92 | 106 | 120 | 134 | 148 | 162 | 7.210 | 7.850 | 7.212 | 0.002 | 7.850 | 0.000 | 1817821 | 0.46% |
| 97 | −8/−10 | 115 | 117 | 129 | 131 | 143 | 145 | 7.210 | 7.850 | 7.212 | 0.002 | 7.850 | 0.000 | 2663527 | 0.67% |
| 98 | −12 | 128 | 141 | 142 | 155 | 156 | 169 | 7.210 | 7.850 | 7.212 | 0.002 | 7.850 | 0.000 | 2245793 | 0.56% |
| 99 | −14/−16 | 151 | 153 | 165 | 167 | 179 | 181 | 7.210 | 7.850 | 7.212 | 0.002 | 7.850 | 0.000 | 2458246 | 0.62% |
| 100 | −18 | 178 | 191 | 192 | 205 | 206 | 219 | 7.210 | 7.850 | 7.212 | 0.002 | 7.850 | 0.000 | 1374209 | 0.35% |
| 101 | −20 | 202 | 215 | 226 | 239 | 228 | 241 | 7.210 | 7.850 | 7.212 | 0.002 | 7.850 | 0.000 | 486389 | 0.12% |
| 102 | nC29 | 43 | 57 | 71 | 85 | 99 | 113 | 7.460 | 7.650 | 7.461 | 0.001 | 7.651 | 0.001 | 6991682 | 1.76% |
| 103 | isoPara | 43 | 57 | 71 | 85 | 99 | 113 | 7.660 | 7.850 | 7.661 | 0.001 | 7.850 | 0.000 | 4955193 | 1.24% |
| 104 | nC30 | 43 | 57 | 71 | 85 | 99 | 113 | 7.850 | 8.000 | 7.850 | 0.000 | 8.000 | 0.000 | 4958373 | 1.25% |
| 105 | isoPara | 43 | 57 | 71 | 85 | 99 | 113 | 8.010 | 8.295 | 8.010 | 0.000 | 8.299 | 0.004 | 6178952 | 1.55% |
| 106 | ½ Ring | 69 | 83 | 97 | 109 | 123 | 137 | 8.010 | 8.650 | 8.010 | 0.000 | 8.659 | 0.009 | 10751285 | 2.70% |
| 107 | ¾ Ring | 149 | 163 | 177 | 189 | 203 | 217 | 8.010 | 8.650 | 8.010 | 0.000 | 8.659 | 0.009 | 1907831 | 0.48% |
| 108 | ⅘ Ring | 229 | 243 | 257 | 269 | 283 | 297 | 8.010 | 8.650 | 8.010 | 0.000 | 8.659 | 0.009 | 196189 | 0.05% |
| 109 | 6 Ring | 309 | 223 | 337 | | | | 8.010 | 8.650 | 8.010 | 0.000 | 8.659 | 0.009 | 127558 | 0.03% |
| 110 | −6 | 91 | 105 | 119 | 133 | 147 | 161 | 8.010 | 8.650 | 8.010 | 0.000 | 8.659 | 0.009 | 3242569 | 0.81% |
| 111 | −6.1 | 92 | 106 | 120 | 134 | 148 | 162 | 8.010 | 8.650 | 8.010 | 0.000 | 8.659 | 0.009 | 1342699 | 0.34% |
| 112 | −8/−10 | 115 | 117 | 129 | 131 | 143 | 145 | 8.010 | 8.650 | 8.010 | 0.000 | 8.659 | 0.009 | 1967623 | 0.49% |
| 113 | −12 | 128 | 141 | 142 | 155 | 156 | 169 | 8.010 | 8.650 | 8.010 | 0.000 | 8.659 | 0.009 | 1667447 | 0.42% |
| 114 | −14/−16 | 151 | 153 | 165 | 167 | 179 | 181 | 8.010 | 8.650 | 8.010 | 0.000 | 8.659 | 0.009 | 1887826 | 0.47% |
| 115 | −18 | 178 | 191 | 192 | 205 | 206 | 219 | 8.010 | 8.650 | 8.010 | 0.000 | 8.659 | 0.009 | 1236165 | 0.31% |
| 116 | −20 | 202 | 215 | 226 | 239 | 228 | 241 | 8.010 | 8.250 | 8.010 | 0.000 | 8.254 | 0.004 | 146569 | 0.04% |
| 117 | nC31 | 43 | 57 | 71 | 85 | 99 | 113 | 8.296 | 8.370 | 8.300 | 0.004 | 8.375 | 0.005 | 2583429 | 0.65% |
| 118 | isoPara | 43 | 57 | 71 | 85 | 99 | 113 | 8.380 | 8.650 | 8.385 | 0.005 | 8.659 | 0.009 | 4469752 | 1.12% |
| 119 | nC32 | 43 | 57 | 71 | 85 | 99 | 113 | 8.660 | 8.790 | 8.669 | 0.009 | 8.801 | 0.011 | 2560156 | 0.64% |
| 120 | isoPara | 43 | 57 | 71 | 85 | 99 | 113 | 8.770 | 8.990 | 8.781 | 0.011 | 9.004 | 0.014 | 2663403 | 0.67% |
| 121 | ½ Ring | 69 | 83 | 97 | 109 | 123 | 137 | 8.770 | 9.450 | 8.781 | 0.011 | 9.470 | 0.020 | 5899868 | 1.48% |
| 122 | ¾ Ring | 149 | 163 | 177 | 189 | 203 | 217 | 8.770 | 9.450 | 8.781 | 0.011 | 9.470 | 0.020 | 954081 | 0.24% |
| 123 | ⅘ Ring | 229 | 243 | 257 | 269 | 283 | 297 | 8.770 | 9.450 | 8.781 | 0.011 | 9.470 | 0.020 | 13230 | 0.00% |
| 124 | 6 Ring | 309 | 223 | 337 | | | | 8.770 | 9.450 | 8.781 | 0.011 | 9.470 | 0.020 | 38830 | 0.01% |
| 125 | −6 | 91 | 105 | 119 | 133 | 147 | 161 | 8.770 | 9.450 | 8.781 | 0.011 | 9.470 | 0.020 | 1859735 | 0.47% |
| 126 | −6.1 | 92 | 106 | 120 | 134 | 148 | 162 | 8.770 | 9.450 | 8.781 | 0.011 | 9.470 | 0.020 | 715807 | 0.18% |
| 127 | 31 8/−10 | 115 | 117 | 129 | 131 | 143 | 145 | 8.770 | 9.450 | 8.781 | 0.011 | 9.470 | 0.020 | 1142789 | 0.29% |
| 128 | −12 | 128 | 141 | 142 | 155 | 156 | 169 | 8.770 | 9.450 | 8.781 | 0.011 | 9.470 | 0.020 | 918741 | 0.23% |
| 129 | −14/−16 | 151 | 153 | 165 | 167 | 179 | 181 | 8.770 | 9.450 | 8.781 | 0.011 | 9.470 | 0.020 | 1136477 | 0.29% |
| 130 | −18 | 178 | 191 | 192 | 205 | 206 | 219 | 8.770 | 9.450 | 8.781 | 0.011 | 9.470 | 0.020 | 845587 | 0.21% |
| 131 | −20 | 202 | 215 | 226 | 239 | 228 | 241 | 8.770 | 9.450 | 8.781 | 0.011 | 9.470 | 0.020 | 91593 | 0.02% |
| 132 | nC33 | 43 | 57 | 71 | 85 | 99 | 113 | 8.950 | 9.110 | 8.963 | 0.013 | 9.125 | 0.015 | 2097419 | 0.53% |
| 133 | isoPara | 43 | 57 | 71 | 85 | 99 | 113 | 9.110 | 9.495 | 9.125 | 0.015 | 9.515 | 0.020 | 3088417 | 0.78% |
| 134 | nC34 | 43 | 57 | 71 | 85 | 99 | 113 | 9.495 | 9.557 | 9.515 | 0.020 | 9.578 | 0.021 | 708383 | 0.18% |
| 135 | isoPara | 43 | 57 | 71 | 85 | 99 | 113 | 9.560 | 9.920 | 9.581 | 0.021 | 9.946 | 0.026 | 1610349 | 0.40% |
| 136 | ½ Ring | 69 | 83 | 97 | 109 | 123 | 137 | 9.560 | 10.510 | 9.581 | 0.021 | 10.544 | 0.034 | 3118811 | 0.78% |
| 137 | ¾ Ring | 149 | 163 | 177 | 189 | 203 | 217 | 9.560 | 10.510 | 9.581 | 0.021 | 10.544 | 0.034 | 300935 | 0.08% |
| 138 | ⅘ Ring | 229 | 243 | 257 | 269 | 283 | 297 | 9.560 | 10.510 | 9.581 | 0.021 | 10.544 | 0.034 | 0 | 0.00% |
| 139 | 6 Ring | 309 | 223 | 337 | | | | 9.560 | 10.510 | 9.580 | 0.021 | 10.544 | 0.034 | 0 | 0.00% |
| 140 | −6 | 91 | 105 | 119 | 133 | 147 | 161 | 9.560 | 10.510 | 9.581 | 0.021 | 10.544 | 0.034 | 1024718 | 0.26% |
| 141 | −6.1 | 92 | 106 | 120 | 134 | 148 | 162 | 9.560 | 10.510 | 9.581 | 0.021 | 10.544 | 0.034 | 236956 | 0.06% |
| 142 | −8/−10 | 115 | 117 | 129 | 131 | 143 | 145 | 9.560 | 10.510 | 9.581 | 0.021 | 10.544 | 0.034 | 464466 | 0.12% |
| 143 | −12 | 128 | 141 | 142 | 155 | 156 | 169 | 9.560 | 10.510 | 9.581 | 0.021 | 10.544 | 0.034 | 310522 | 0.08% |
| 144 | −14/−16 | 151 | 153 | 165 | 167 | 179 | 181 | 9.560 | 10.510 | 9.581 | 0.021 | 10.544 | 0.034 | 497830 | 0.13% |
| 145 | −18 | 178 | 191 | 192 | 205 | 206 | 219 | 9.560 | 10.510 | 9.581 | 0.021 | 10.544 | 0.034 | 188335 | 0.05% |
| 146 | −20 | 202 | 215 | 226 | 239 | 228 | 241 | 9.560 | 10.510 | 9.581 | 0.021 | 10.544 | 0.034 | 0 | 0.00% |

COMPLETE CHEMIST'S RULES FOR LUBES

Total Raw Abundance (TIC): 770247450
Chemist Rule: 398341548  −51.72%
Air Leakage: 247241  −0.03%
Avg Scan Rate (Min/Max): 292 (292/293)
Number of Records: 2864

| Rule[a] | Compound[b] | Masses[c] | | | | | | Start[d] | End[e] | CStart[f] | Corr[g] | CEnd[h] | Corr[i] | Abundance[j] | |
|---|---|---|---|---|---|---|---|---|---|---|---|---|---|---|---|
| 147 | nC35 | 43 | 57 | 71 | 85 | 99 | 113 | 9.930 | 10.040 | 9.956 | 0.026 | 10.068 | 0.028 | 761456 | 0.19% |
| 148 | isoPara | 43 | 57 | 71 | 85 | 99 | 113 | 10.040 | 10.510 | 10.068 | 0.028 | 10.544 | 0.034 | 1221984 | 0.31% |
| 149 | nC36 | 43 | 57 | 71 | 85 | 99 | 113 | 10.510 | 10.670 | 10.544 | 0.034 | 10.705 | 0.035 | 406119 | 0.10% |
| 150 | isoPara | 43 | 57 | 71 | 85 | 99 | 113 | 10.670 | 11.160 | 10.705 | 0.035 | 11.195 | 0.035 | 649097 | 0.16% |
| 151 | ½ Ring | 69 | 83 | 97 | 109 | 123 | 137 | 10.670 | 11.930 | 10.705 | 0.035 | 11.965 | 0.035 | 1248714 | 0.31% |
| 152 | ¾ Ring | 149 | 163 | 177 | 189 | 203 | 217 | 10.670 | 11.930 | 10.705 | 0.035 | 11.965 | 0.035 | 1039 | 0.00% |
| 153 | ⅘ Ring | 229 | 243 | 257 | 269 | 283 | 297 | 10.670 | 11.930 | 10.705 | 0.035 | 11.965 | 0.035 | 0 | 0.00% |
| 154 | 6 Ring | 309 | 223 | 337 | | | | 10.670 | 11.930 | 10.705 | 0.035 | 11.965 | 0.035 | 0 | 0.00% |
| 155 | −6 | 91 | 105 | 119 | 133 | 147 | 161 | 10.670 | 11.930 | 10.705 | 0.035 | 11.965 | 0.035 | 184368 | 0.05% |
| 156 | −6.1 | 92 | 106 | 120 | 134 | 148 | 162 | 10.670 | 11.930 | 10.705 | 0.035 | 11.965 | 0.035 | 0 | 0.00% |
| 157 | −8/−10 | 115 | 117 | 129 | 131 | 143 | 145 | 10.670 | 11.930 | 10.705 | 0.035 | 11.965 | 0.035 | 6320 | 0.00% |
| 158 | −12 | 128 | 141 | 142 | 155 | 156 | 169 | 10.670 | 11.930 | 10.705 | 0.035 | 11.965 | 0.035 | 0 | 0.00% |
| 159 | −14/−16 | 151 | 153 | 165 | 167 | 179 | 181 | 10.670 | 11.930 | 10.705 | 0.035 | 11.965 | 0.035 | 6298 | 0.00% |
| 160 | −18 | 178 | 191 | 192 | 205 | 206 | 219 | 10.670 | 11.930 | 10.705 | 0.035 | 11.965 | 0.035 | 14900 | 0.00% |
| 161 | −20 | 202 | 215 | 226 | 239 | 228 | 241 | 10.670 | 11.930 | 10.705 | 0.035 | 11.965 | 0.035 | 0 | 0.00% |
| 162 | nC37 | 43 | 57 | 71 | 85 | 99 | 113 | 11.170 | 11.280 | 11.205 | 0.035 | 11.315 | 0.035 | 166702 | 0.04% |
| 163 | isoPara | 43 | 57 | 71 | 85 | 99 | 113 | 11.290 | 11.930 | 11.325 | 0.035 | 11.965 | 0.035 | 446488 | 0.11% |
| 164 | nC38 | 43 | 57 | 71 | 85 | 99 | 113 | 11.940 | 12.060 | 11.975 | 0.035 | 12.095 | 0.035 | 78001 | 0.02% |
| 165 | isoPara | 43 | 57 | 71 | 85 | 99 | 113 | 12.070 | 12.830 | 12.105 | 0.035 | 12.865 | 0.035 | 259052 | 0.07% |
| 166 | ½ Ring | 69 | 83 | 97 | 109 | 123 | 137 | 12.070 | 14.000 | 12.105 | 0.035 | 14.035 | 0.035 | 195191 | 0.05% |
| 167 | ¾ Ring | 149 | 163 | 177 | 189 | 203 | 217 | 12.070 | 14.000 | 12.105 | 0.035 | 14.035 | 0.035 | 0 | 0.00% |
| 168 | ⅘ Ring | 229 | 243 | 257 | 269 | 283 | 297 | 12.070 | 14.000 | 12.105 | 0.035 | 14.035 | 0.035 | 0 | 0.00% |
| 169 | 6 Ring | 309 | 223 | 337 | | | | 12.070 | 14.000 | 12.105 | 0.035 | 14.035 | 0.035 | 0 | 0.00% |
| 170 | −6 | 91 | 105 | 119 | 133 | 147 | 161 | 12.070 | 14.000 | 12.105 | 0.035 | 14.035 | 0.035 | 0 | 0.00% |
| 171 | −6.1 | 92 | 106 | 120 | 134 | 148 | 162 | 12.070 | 14.000 | 12.105 | 0.035 | 14.035 | 0.035 | 0 | 0.00% |
| 172 | −8/−10 | 115 | 117 | 129 | 131 | 143 | 145 | 12.070 | 14.000 | 12.105 | 0.035 | 14.035 | 0.035 | 0 | 0.00% |
| 173 | −12 | 128 | 141 | 142 | 155 | 156 | 169 | 12.070 | 14.000 | 12.105 | 0.035 | 14.035 | 0.035 | 0 | 0.00% |
| 174 | −14/−16 | 151 | 153 | 165 | 167 | 179 | 181 | 12.070 | 14.000 | 12.105 | 0.035 | 14.035 | 0.035 | 0 | 0.00% |
| 175 | −18 | 178 | 191 | 192 | 205 | 206 | 219 | 12.070 | 14.000 | 12.105 | 0.035 | 14.035 | 0.035 | 0 | 0.00% |
| 176 | −20 | 202 | 215 | 226 | 239 | 228 | 241 | 12.070 | 14.000 | 12.105 | 0.035 | 14.035 | 0.035 | 0 | 0.00% |
| 177 | nC39 | 43 | 57 | 71 | 85 | 99 | 113 | 12.830 | 12.870 | 12.865 | 0.035 | 12.905 | 0.035 | 7911 | 0.00% |
| 178 | isoPara | 43 | 57 | 71 | 85 | 99 | 113 | 12.880 | 14.000 | 12.915 | 0.035 | 14.035 | 0.035 | 106764 | 0.03% |
| | | | | | | | | | | Sum = | | | | 398341548 | 100.00% |

[a] Rule number, integer index.
[b] Compound or group of compound rule applies to:
½ ring  ½ ring cycloparaffins
¾ ring  ¾ ring cycloparaffins
⅘ ring  ⅘ ring cycloparaffins
6 ring  6 ring cycloparaffins
−6  $C_nH_{2n-6}$ alkylated benzenes
−6.1  $C_nH_{2n-6}$ linear alkylated benzenes
−8/−10  $C_nH_{2n-8}$ alkylated indanes, $C_nH_{2n-10}$ alkylated indenes
−12  $C_nH_{2n-12}$ alkylated naphthalenes
−14/16  $C_nH_{2n-14}$ alkylated acenaphthenes/$C_nH_{2n-16}$ alkylated acenaphthalenes
−18  $C_nH_{2n-18}$ alkylated phenanthrenes/anthracenes
−20  $C_nH_{2n-20}$ alkylated naphthenophenanthrenes
[c] Masses used in Rule [up to n may be specified, where n is an integer which is equal to the number of masses scanned during the time interval (d to e) either in full scan mode or selected ion monitoring mode].
[d] Retention time for both starting and ending expected retention times based on historical averages in minutes.
[e] End retention time in minutes.
[f] Corrected start retention time.
[g] Correction = difference between start and cstart (in minutes).
[h] Corrected end time
[i] Correction = Difference between end and cend (in minutes)
[j] Abundance, both as total sum and as normalized percentage based on Chemist's Rule.

What is claimed is:

1. A process for controlling the manufacture of lubricating oils from a feed having a boiling point of about 350° C. or greater by the steps of introducing the feed into a distillation unit, separating the feed into light, medium and heavy distillates, introducing the distillates into an extraction unit, extracting the distillates to produce raffinates, introducing the raffinates into a dewaxing unit and dewaxing the raffinates to produce lubricating oils, said process comprising:

(a) obtaining samples of at least one lubricating oil, feed, distillate and raffinate;

(b) selecting at least one physical, chemical, perceptual or performance properties of at least one of lubricating oil, feed, distillate and raffinate;

(c) selecting reference samples, said reference samples containing characteristic compound types present in the at least one lubricating oil, feed, distillate and raffinate and which have known values for the property or properties selected in step (b);

(d) producing a training set by the steps of:

(1) injecting each reference sample into a gas chromatograph which is interfaced to a mass spectrometer thereby causing at least a partial separation of the hydrocarbon mixture into constituent chemical components;

(2) introducing the constituent chemical components of each reference sample into the mass spectrometer, under dynamic flow conditions;

(3) obtaining for each reference sample a series of time resolved mass chromatograms;

(4) calibrating the mass chromatograms to correct retention times;

(5) selecting a series of corrected retention time windows;

(6) selecting within each retention time window a series of molecular and/or fragment ions, said ions being representative of characteristic compounds or compound classes expected within the retention time window;

(7) recording the total amount of each characteristic compound or compound group selected in step d(6);

(8) forming the data from steps d(6) and d(7) into a X-block matrix;

(9) forming the property data selected in (b) for reference samples selected in (c) into a Y-block matrix;

(10) analyzing the data from steps d(8) and d(9) by multivariate correlation techniques such as Partial Least Squares, Principal Component Regression or Ridge Regression to produce a series of coefficients;

(e) subjecting at least one unknown sample of at least one of lubricating oil, feed, distillate and raffinate to the steps d(1) to d(3) in the same manner as the reference samples to produce a series of time resolved mass chromatograms;

(f) repeating steps d(4) and d(8) for each mass chromatogram from step (e);

(g) multiplying the matrix from step (f) by the coefficients from step d(10) to produce a predicted value for the property or properties for the at least one lubricating oil, feed, distillate and raffinate sample or samples; and (h) using the predicted values of the property or properties of the at least one lubricating oil, feed, distillate and raffinate sample or samples to control operation of at least one of the distillation unit, extraction unit and dewaxing unit.

2. A method for controlling or monitoring chemical or refinery processes which utilize feedstocks and/or produce products having boiling points greater than about 350° C. which comprises:

(a) obtaining at least one sample of a refinery or chemical feedstock or product;

(b) selecting at least one physical, chemical, perceptual or performance property of at least one refinery or chemical process feedstock or product;

(c) selecting reference samples, said reference samples containing characteristic compound types present in the at least one refinery or chemical process feedstock or products and which have known values for the property or properties selected in step (b);

(d) producing a training set by the steps of:

(1) injecting each reference sample into a gas chromatograph which is interfaced to a mass spectrometer thereby causing at least a partial separation of the hydrocarbon mixture into constituent chemical components;

(2) introducing the constituent chemical components of each reference sample into the mass spectrometer, under dynamic flow conditions;

(3) obtaining for each reference sample a series of time resolved mass chromatograms;

(4) calibrating the mass chromatograms to correct retention times;

(5) selecting a series of corrected retention time windows;

(6) selecting within each retention time window a series of molecular and/or fragment ions, said ions being representative of characteristic compounds or compound classes expected within the retention time window;

(7) recording the total amount of each characteristic compound or compound group selected in step d(6);

(8) forming the data from steps d(6) and d(7) into a X-block matrix;

(9) forming the property data selected in (b) for reference samples selected in (c) into a Y-block matrix;

(10) analyzing the data from steps d(8) and d(9) by multivariate correlation techniques such as Partial Least Squares, Principal Component Regression or Ridge Regression to produce a series of coefficients;

(e) subjecting at least one unknown refinery or chemical process feedstock or process sample to steps d(1) to d(3) in the same manner as the reference samples to produce a series of time resolved mass chromatograms;

(f) repeating steps d(4) and d(8) for each mass chromatogram from step (e);

(g) multiplying the matrix from step (f) by the coefficients from step d(10) to produce a predicted value for the property or properties for the refinery or chemical process feedstocks or products sample or samples; and (h) using the predicted values of the property or properties of the refinery or chemical feed stocks or products sample or samples to control the refinery or chemical process.

3. The method of claims 1 or 2 wherein the gas chromatograph is a capillary gas chromatograph and the mass spectrometer is a quadrupole mass spectrometer.

4. The method of claims 1 or 2 wherein the gas chromatograph and mass spectrometer are operated under repeatable conditions.

5. The method of claims 1 or 2 wherein the selection of a series of molecular and/or fragment ions characteristic of compounds or compound classes is accomplished using Chemist's Rules.

6. The method of claims 1 or 2 wherein the selection of a series of molecular and/or fragment ions characteristic of compounds or compound classes is accomplished using Hydrocarbon Type Analysis.

7. The method of claims 1 or 2 wherein data from the gas chromatograph and mass spectrometer are stored in a computer.

8. The method of claims 1 or 2 wherein data from steps (c) and (g) are treated in a computer.

9. The method of claims 1 or 2 wherein other chemical performance, perceptual or physical properties of the hydrocarbon mixture are selected.

10. The method of claims 1 or 2 wherein the data are collinear.

11. The method of claims 1 or 2 wherein the multivariate correlation technique is Partial Least Squares.

* * * * *